(12) United States Patent
McAlister

(10) Patent No.: US 8,312,759 B2
(45) Date of Patent: Nov. 20, 2012

(54) METHODS, DEVICES, AND SYSTEMS FOR DETECTING PROPERTIES OF TARGET SAMPLES

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/027,188

(22) Filed: Feb. 14, 2011

(65) Prior Publication Data
US 2011/0197662 A1 Aug. 18, 2011

Related U.S. Application Data

(63) Continuation-in-part of application No. 12/806,634, filed on Aug. 16, 2010, which is a continuation-in-part of application No. 12/707,651, filed on Feb. 17, 2010, now Pat. No. 8,075,748, and a continuation-in-part of application No. PCT/US2010/024497, filed on Feb. 17, 2010, and a continuation-in-part of application No. 12/707,653, filed on Feb. 17, 2010, now Pat. No. 8,172,990, and a continuation-in-part of application No. PCT/US2010/024498, filed on Feb. 17, 2010, and a continuation-in-part of application No. 12/707,656, filed on Feb. 17, 2010, now Pat. No. 8,075,749, and a continuation-in-part of application No. PCT/US2010/024499, filed on Feb. 17, 2010.

(60) Provisional application No. 61/304,403, filed on Feb. 13, 2010, provisional application No. 61/153,253, filed on Feb. 17, 2009, provisional application No. 61/237,476, filed on Aug. 27, 2009.

(51) Int. Cl.
*G01N 30/00* (2006.01)

(52) U.S. Cl. .............. 73/31.07; 73/28.01; 73/28.04; 73/31.01; 73/31.03; 73/31.05

(58) Field of Classification Search ............ 73/23.2, 73/23.3, 23.31, 23.32, 28.01, 28.04, 31.01, 73/31.02, 31.03, 31.05, 31.07
See application file for complete search history.

(56) References Cited

U.S. PATENT DOCUMENTS
5,475,772 A 12/1995 Hung et al.
(Continued)

FOREIGN PATENT DOCUMENTS
WO WO 2009035647 A1 * 3/2009
(Continued)

OTHER PUBLICATIONS

Emery, Chris. "Princeton Engineers Make Breakthrough in Untra-Sensitive Sensor." Princeton School of Engineering and Applied Science, Published: Mar. 23, 2011. Accessed: May 18, 2011. <http://www.princeton.edu/engineering/news/archive/?id=4867>. pp. 1-4.

(Continued)

*Primary Examiner* — David Rogers
(74) *Attorney, Agent, or Firm* — Susan D. Betcher

(57) ABSTRACT

Systems and methods for collecting portions of a target sample are disclosed herein. A method for detecting the presence and/or properties of a target sample can include selectively collecting a portion of a target sample with a sample collector and detecting, with the sample collector, the presence of one or more properties of the microscopic portion of the target sample. The method also includes analyzing, with the sample collector, the one or more properties of the microscopic portion of the target sample. Based on the analysis, the method further includes reporting, from the sample collector, a real-time indication of the analysis of the one or more properties of the target sample. The method can also include at least partially removing the microscopic portion of the target sample from the sample collector. The methods and systems disclosed herein can be used, for example, in systems or environments directed to quality assurance, preventative maintenance, safety, hazard warnings, homeland security, chemical identification and surveillance, and/or other suitable environments.

18 Claims, 18 Drawing Sheets

U.S. PATENT DOCUMENTS

| | | |
|---|---|---|
| 5,882,044 A | 3/1999 | Sloane |
| 5,969,618 A | 10/1999 | Redmond |
| 6,185,355 B1 | 2/2001 | Hung |
| 6,386,596 B1 | 5/2002 | Olson |
| 6,446,597 B1 | 9/2002 | McAlister |
| 6,532,315 B1 | 3/2003 | Hung et al. |
| 6,567,599 B2 | 5/2003 | Hung |
| 6,583,901 B1 | 6/2003 | Hung |
| 6,584,244 B2 | 6/2003 | Hung |
| 6,587,239 B1 | 7/2003 | Hung |
| 6,652,006 B1 | 11/2003 | Digiacomo |
| D505,681 S | 5/2005 | Rossman et al. |
| 7,108,296 B2 | 9/2006 | Andre |
| 7,134,323 B1 * | 11/2006 | Discenzo .................. 73/53.05 |
| 7,257,984 B2 * | 8/2007 | Pidria et al. ................... 73/10 |
| 7,287,412 B2 * | 10/2007 | Ng et al. ..................... 73/23.31 |
| 7,658,901 B2 * | 2/2010 | Prud'Homme et al. ... 423/415.1 |
| 7,692,553 B2 | 4/2010 | Kubala |
| 7,765,854 B2 * | 8/2010 | Schilowitz et al. ......... 73/64.53 |
| 7,802,466 B2 * | 9/2010 | Whalen et al. ............... 73/54.41 |
| 7,823,450 B2 | 11/2010 | Sugibayashi |
| 7,825,568 B2 | 11/2010 | Andle |
| 7,870,787 B2 | 1/2011 | Harigai et al. |
| 7,885,785 B1 | 2/2011 | Pekarek et al. |
| 7,900,512 B2 | 3/2011 | Kano et al. |
| 7,902,730 B2 | 3/2011 | Shibata et al. |
| 7,905,209 B2 | 3/2011 | Goto et al. |
| 7,908,661 B2 | 3/2011 | Silverbrook et al. |
| 2002/0084793 A1 | 7/2002 | Hung et al. |
| 2002/0131171 A1 | 9/2002 | Hung |
| 2002/0131666 A1 | 9/2002 | Hung et al. |
| 2002/0131673 A1 | 9/2002 | Hung |
| 2002/0131674 A1 | 9/2002 | Hung |
| 2002/0131686 A1 | 9/2002 | Hung |
| 2002/0131706 A1 | 9/2002 | Hung |
| 2002/0131756 A1 | 9/2002 | Hung |
| 2002/0141692 A1 | 10/2002 | Hung |
| 2002/0150375 A1 | 10/2002 | Hung et al. |
| 2002/0151113 A1 | 10/2002 | Hung et al. |
| 2004/0008989 A1 | 1/2004 | Hung |
| 2007/0160842 A1 * | 7/2007 | Hirata et al. .................. 428/408 |
| 2008/0048448 A1 | 2/2008 | Jamison et al. |
| 2009/0235721 A1 * | 9/2009 | Robinson et al. ........... 73/31.05 |
| 2009/0242405 A1 * | 10/2009 | Mayer et al. .................. 204/435 |
| 2010/0173422 A1 * | 7/2010 | Koley et al. .................. 436/149 |
| 2010/0273060 A1 * | 10/2010 | Yang et al. .................. 429/231.8 |
| 2011/0244585 A1 * | 10/2011 | Mayne-L'Hermite et al. . 436/93 |
| 2012/0086439 A1 * | 4/2012 | Bratkovski et al. ........... 324/204 |
| 2012/0156424 A1 * | 6/2012 | Chen et al. .................... 428/119 |
| 2012/0206012 A1 * | 8/2012 | Rosenblatt et al. ........... 310/300 |

FOREIGN PATENT DOCUMENTS

WO    WO 2011004136 A1 *    1/2011

OTHER PUBLICATIONS

Steele, Bill. "Carbon Nanotube Oscillator." Cornell Chronicle Online. Published: Sep. 15, 2004. Accessed: Nov. 24, 2008. Printed: Jun. 13, 2011 <http://www.news.cornell.edu/releases/Sept04/McEuen.nanotube.ws.html>.

Yablonobitch, E. "Photonic Bandgap Based Designs for Nano-Photonic Integrated Circuits." IEEE International Electron Devices Meeting 2002 (IEDM '02). 2002. pp. 17-20.

International Search Report and Written Opinion for PCT Application No. PCT/US11/24798; Mailed on Oct. 31, 2011; Applicant: McAlister Technologies, LLC; 10 Pages.

* cited by examiner

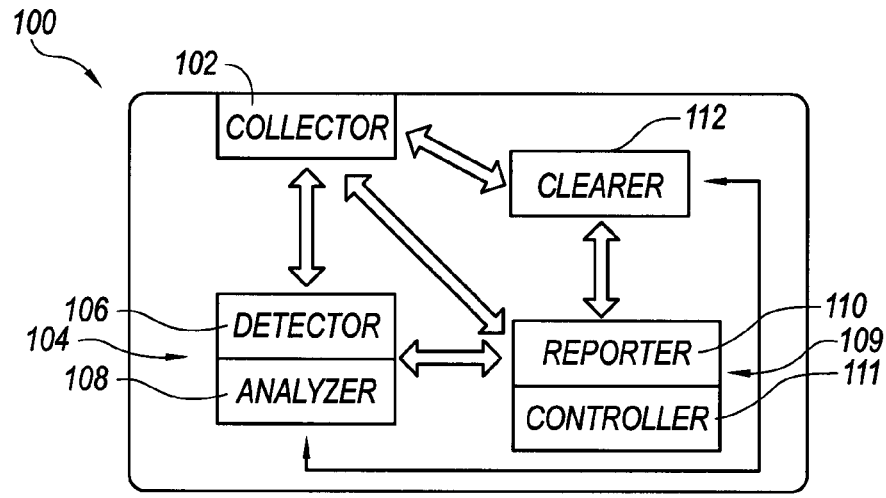
Fig. 1
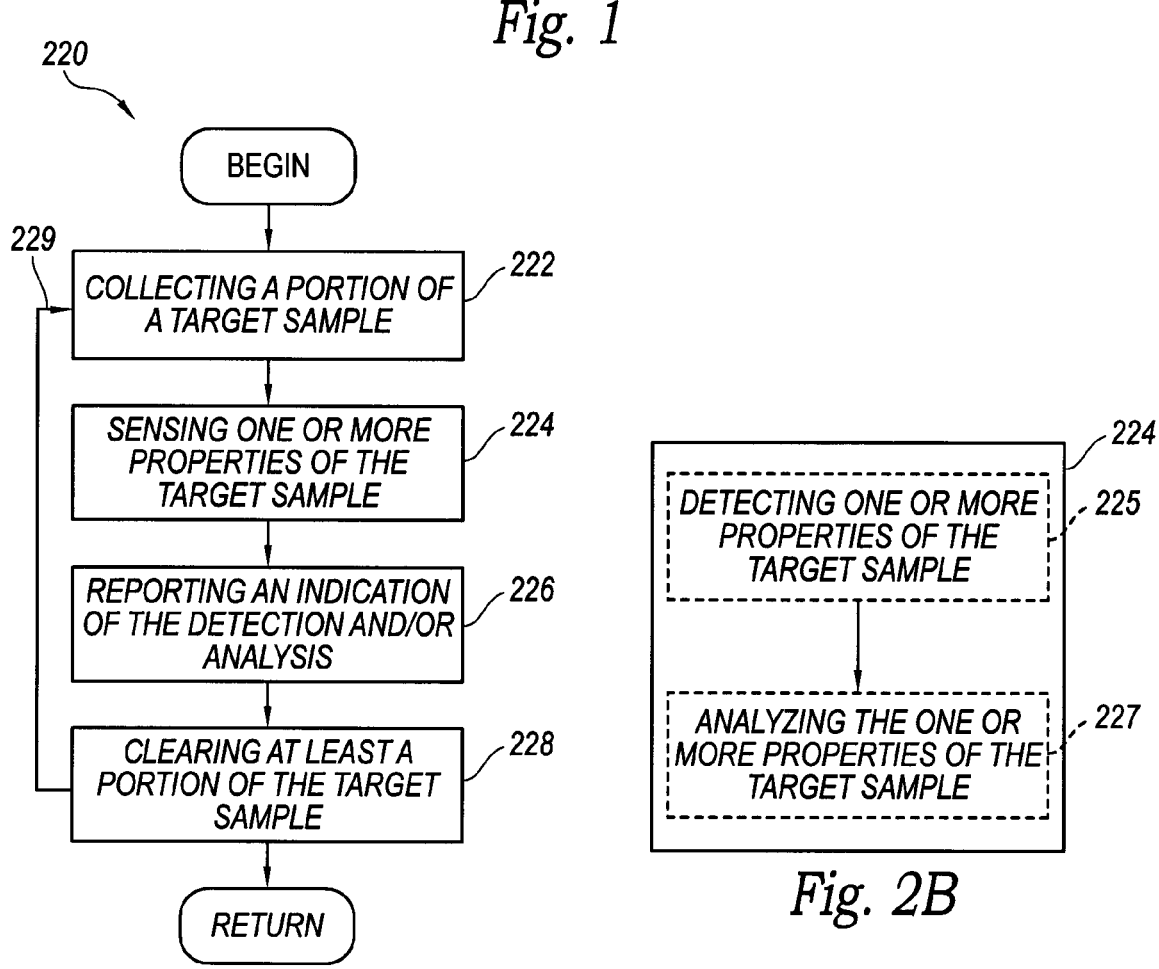
Fig. 2A
Fig. 2B

METHODS, DEVICES, AND SYSTEMS FOR DETECTING PROPERTIES OF TARGET SAMPLES

CROSS-REFERENCE TO RELATED APPLICATIONS

The present application claims priority to and the benefit of U.S. Patent Application No. 61/304,403, filed on Feb. 13, 2010 and titled FULL SPECTRUM ENERGY AND RESOURCE INDEPENDENCE. The present application is a continuation in part of U.S. patent application Ser. No. 12/806,634, filed on Aug. 16, 2010 and titled METHODS AND APPARATUSES FOR DETECTION OF PROPERTIES OF FLUID CONVEYANCE SYSTEMS, which claims priority to and the benefit of U.S. Provisional Application No. 61/304,403, filed Feb. 13, 2010 and titled FULL SPECTRUM ENERGY AND RESOURCE INDEPENDENCE. U.S. patent application Ser. No. 12/806,634 is also a continuation-in-part of each of the following applications: U.S. patent application Ser. No. 12/707,651, filed Feb. 17, 2010 and titled ELECTROLYTIC CELL AND METHOD OF USE THEREOF; PCT Application No. PCT/US10/24497, filed Feb. 17, 2010 and titled ELECTROLYTIC CELL AND METHOD OF USE THEREOF; U.S. patent application Ser. No. 12/707,653, filed Feb. 17, 2010 and titled APPARATUS AND METHOD FOR CONTROLLING NUCLEATION DURING ELECTROLYSIS; PCT Application No. PCT/US10/24498, filed Feb. 17, 2010 and titled APPARATUS AND METHOD FOR CONTROLLING NUCLEATION DURING ELECTROLYSIS; U.S. patent application Ser. No. 12/707,656, filed Feb. 17, 2010 and titled APPARATUS AND METHOD FOR GAS CAPTURE DURING ELECTROLYSIS; and PCT Application No. PCT/US10/24499, filed Feb. 17, 2010 and titled APPARATUS AND METHOD FOR CONTROLLING NUCLEATION DURING ELECTROLYSIS; each of which claims priority to and the benefit of the following applications: U.S. Provisional Patent Application No. 61/153,253, filed Feb. 17, 2009 and titled FULL SPECTRUM ENERGY; U.S. Provisional Patent Application No. 61/237,476, filed Aug. 27, 2009 and titled ELECTROLYZER AND ENERGY INDEPENDENCE TECHNOLOGIES; U.S. Provisional Application No. 61/304,403, filed Feb. 13, 2010 and titled FULL SPECTRUM ENERGY AND RESOURCE INDEPENDENCE. Each of these applications is incorporated herein by reference in its entirety. To the extent the foregoing application and/or any other materials incorporated herein by reference conflict with the disclosure presented herein, the disclosure herein controls.

TECHNICAL FIELD

The present disclosure is directed generally to methods, devices, and systems for detecting the presence and/or properties of a portion of a target sample.

BACKGROUND

Fittings are used to connect two objects, such as, for example, a tube and a device that facilitates fluid communication with the tube. One example of such a device is a valve. Fittings may also be utilized to cap or plug an opening or aperture. Additionally, fittings must maintain a seal against leakage while meeting various design criteria relating to, for example, pressure, temperature, and vibration.

It may be advantageous to provide for early detection of conditions that could cause a leak or the incipient leak conditions for the purpose of instituting fail-safe operations and/or preventative maintenance.

Presently, connections between fittings may be susceptible to leakage. Leakage may cause hazardous conditions due to the escape of oxidants, odorants, pharmaceutical fluids, fuels, poisonous substances or otherwise objectionable or undesirable substances. Leakage may cause loss of valuable substances or the interruption of processes involving the accurate and adequate delivery of certain substances. In addition to degradation of an O-ring or gasket forming a seal between the fittings, leakage may result from mechanical loosening of the connection. One typical cause of loosening may be thermal cycling or vibration of a system comprising the fittings.

SUMMARY

Embodiments of the disclosure described herein are directed generally to methods, devices, apparatuses, systems, etc. for monitoring and/or detecting one or more properties of a sample of a target material. Certain embodiments of the disclosure, for example, are directed to collecting a sufficient amount of a target sample, detecting the presence of the portion of the target sample and/or analyzing properties of the target sample, reporting an indication of the detection and/or analysis, and optionally clearing the target sample to enable repeated or cyclic collection of additional samples. As explained in detail below, the amount of the sample that can be collected and analyzed can be a very small or miniscule portion of the target sample including, for example, a molecular or microscopic portion of the target sample. Based on one or more factors related to the presence of the target sample or the properties of the target sample, the methods, devices, and systems disclosed herein can provide an indication of a suitable action or process in response to the detection and/or analysis. A networked array of the systems and sensors as described herein can be used in various suitable environments including, for example, environments directed to quality assurance, preventative maintenance, safety (including trend analysis), hazard warnings (including shut down procedures), chemical identification and surveillance, environmental monitoring, and/or homeland security.

In certain embodiments, for example, systems described herein perform provide an indication of the need of maintenance or other corrective action in response to a detected target sample, as well as the location and/or concentration of an undesired sample or properties. In other embodiments, the systems described herein can provide a gating event related to the detected properties or presence of the target sample. For example, in one embodiment, a system can prevent a certain fluid (e.g., medication, fuel, etc.) from being dispensed if the system detects undesired properties or ingredients in the fluid, including, for example, the wrong fluid. As described in detail below, the methods, devices, systems etc. of the present disclosure utilize several different methods to detect and/or analyze the target sample presence or properties, and to relay or otherwise provide information related to the detected target sample presence or properties. Accordingly, the present disclosure is directed to various different applications including, for example, medication delivery, fuel delivery, tire pressure regulation, pressurized supplies of hydrogen and/or oxygen, safety systems for automotive and trucking industries, tracking systems for international and national shipping, safety systems for natural gas grids, storage tanks and pipelines, homeland security including hazard warnings, wide-area network linking arrays of sensors for airports, public buildings, hospitals, public transportation systems, police identification of drug trafficking, military identification of hazards, EPA identification of industrial polluters, emission reporting, carbon credit tracking and reporting, food chain transport, medical delivery and monitoring applications, etc. Moreover, the systems and methods described herein provide adaptive management and control for real-time and cyclical collecting, analyzing, and reporting one or more properties of a target sample.

BRIEF DESCRIPTION OF THE DRAWINGS

FIG. 1 is a schematic diagram of a system or sensor configured in accordance with an embodiment of the disclosure.

FIG. 2A is a flow diagram of a method configured in accordance with an embodiment of the disclosure.

FIG. 2B is a flow diagram of a portion of the method illustrated in FIG. 2A and configured in accordance with an embodiment of the disclosure.

DETAILED DESCRIPTION

Figure 3A:
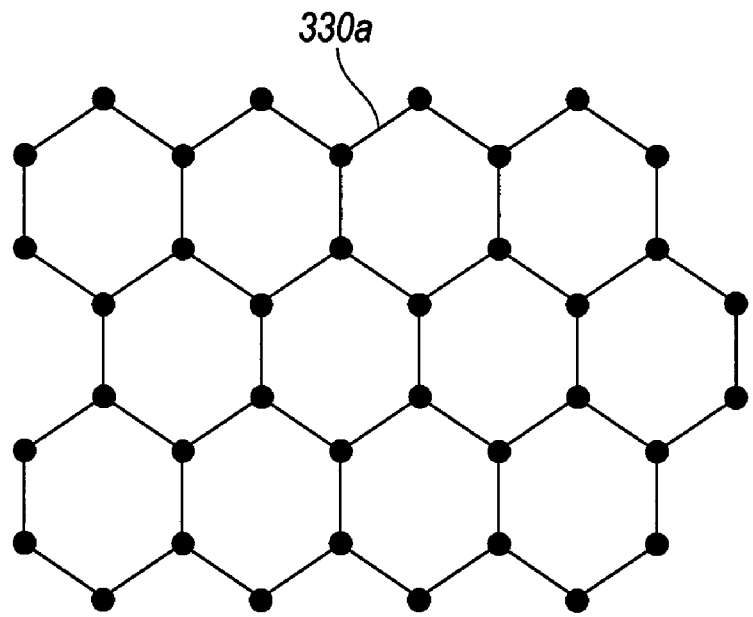
FIG. 3A is a schematic molecular diagram and FIG. 3B is a schematic diagram of stacked sheets illustrating a molecular structure of layers of matrix characterization of crystals configured in accordance with an embodiment of the disclosure.

The present application incorporates by reference in its entirety the subject matter of U.S. Provisional Patent Application No. 60/626,021, filed Nov. 9, 2004 and titled MULTI-FUEL STORAGE, METERING AND IGNITION SYSTEM.

The present application incorporates by reference in their entirety the subject matter of each of the following U.S. Patent Applications, filed on Aug. 16, 2010 and titled:

U.S. Provisional Patent Application No. 60/401,699, COMPREHENSIVE COST MODELING OF AUTOGENOUS SYSTEMS AND PROCESSES FOR THE PRODUCTION OF ENERGY, MATERIAL RESOURCES AND NUTRIENT REGIMES;

U.S. patent application Ser. No. 12/806,633, ELECTROLYTIC CELL AND METHOD OF USE THEREOF;

U.S. patent application Ser. No. 12/857,553, SUSTAINABLE ECONOMIC DEVELOPMENT THROUGH INTEGRATED PRODUCTION OF RENEWABLE ENERGY, MATERIALS RESOURCES, AND NUTRIENT REGIMES;

U.S. patent application Ser. No. 12/857,554, SYSTEMS AND METHODS FOR SUSTAINABLE ECONOMIC DEVELOPMENT THROUGH INTEGRATED FULL SPECTRUM PRODUCTION OF RENEWABLE ENERGY;

U.S. patent application Ser. No. 12/857,541, SUSTAINABLE ECONOMIC DEVELOPMENT THROUGH INTEGRATED FULL SPECTRUM PRODUCTION OF RENEWABLE MATERIAL RESOURCES;

U.S. patent application Ser. No. 12/857,546, INCREASING THE EFFICIENCY OF SUPPLEMENTED OCEAN THERMAL ENERGY CONVERSION (SOTEC);

U.S. patent application Ser. No. 12/857,228, GAS HYDRATE CONVERSION SYSTEM FOR HARVESTING HYDROCARBON HYDRATE DEPOSITS;

U.S. patent application Ser. No. 12/857,515, APPARATUSES AND METHODS FOR STORING AND/OR FILTERING A SUBSTANCE;

U.S. patent application Ser. No. 12/857,502, ENERGY SYSTEM FOR DWELLING SUPPORT;

U.S. patent application Ser. No. 12/857,433, ENERGY CONVERSION ASSEMBLIES AND ASSOCIATED METHODS OF USE AND MANUFACTURE; and U.S. patent application Ser. No. 12/857,461, INTERNALLY REINFORCED STRUCTURAL COMPOSITES AND ASSOCIATED METHODS OF MANUFACTURING.

A. Overview of Embodiments Directed to Methods and Systems for Collecting, Sensing, Reporting, and/or Clearing Portions of a Target Sample Methods, devices, apparatuses, systems, and associated components for providing information relating to certain properties and/or the presence of a target sample are described herein. In certain embodiments, these methods and systems provide a "tattletale" or other type of feedback indication related to properties of a target sample, conditions of the target sample, presence of the target sample, and/or any other applicable properties or characteristics associated with the target sample. As used herein, the term target sample can include any material that is desired or intended to be detected and/or analyzed, including microscopic, molecular, or atomic portions of the material. Moreover, the term fluid as used herein is intended to describe any type of flowable material, including, for example, liquids, gases, plasmas, etc.

In certain embodiments, the methods, systems, and associated components disclosed herein provide an indication of the presence of a target sample, and/or of certain properties regarding the target sample. In one embodiment, for example, the systems and methods disclosed herein can detect and provide an indication that a target sample such as a fluid is leaking from a system that is transporting the fluid. More specifically, the methods and systems can include sensors or indicators that determine when a leak is occurring and provide an indication, such as a signal or an alarm that the fluid is leaking. Moreover, as described in detail below, the indication of the leak (or detection of the presence or other properties of the target sample) can be provided at the very early stage or incipient (e.g., molecular or atomic) levels of the leakage. Moreover, the methods and systems described herein can detect the leakage in response to an interrogation signal directed at the sensor or indicator. In this manner, the embodiments described herein can provide an early detection to an undesirable leak, or any other property or condition associated with a target sample.

Thus, instead of waiting for an odorant in natural gas or propane to infiltrate the atmosphere of a dwelling before an unsuspecting person wakes up and happens to not have a head cold and perchance smells the "rotten-egg" odor and becomes consciously alarmed, the present disclosure provides for prevention of such delays by providing an indication or alarm at the incipient leak or other detection stage. In certain embodiments, the methods and systems can determine the incipient detection with a comparatively miniscule number of molecules of the target sample that have been collected or otherwise accumulated, such as passing a seal for example, and therefore causing an immediate alarm and/or request for maintenance. Moreover, the degree of urgency and corresponding appropriate response can be conditioned according to the trend indicated by collection-rate analysis and comparative evaluation of the particular chemistry involved. If the system detects a collection rate of a sufficient magnitude, for example, the system may provide an indication that immediate maintenance or other action is required. If the system detects a collection rate below a predetermined magnitude, however, the system may provide an indication that the presence or other properties of the target sample exist, but that immediate maintenance may not be required. In addition, and as explained in detail below with reference to embodiments of the disclosure, a system can detect, analyze, or otherwise measure certain properties of the target sample to determine a gating event for flow of the target sample (e.g., flow of a fluid). For example, if the system detects impurities in a fuel, or if the system detects the wrong type of fluid, the system may stop the fuel from flowing or change the flow rate of the fluid.

FIG. 1 is a schematic diagram of a system 100 configured in accordance with an embodiment of the disclosure. As explained in detail below, the system 100 can be a stand-alone sensor or detector that includes multiple components or portions that are configured for sensing the presence and/or properties of one or more target samples, and providing an indication of the sensing of the target sample. More specifically, the system 100 includes a collector portion 102 and a sensing portion 104. In certain embodiments the sensing portion 106 can include a detector portion 106 as well as an analyzing portion 108. The system 100 further includes a communication or control portion 110 and a clearer portion 112. In certain embodiments, the communication or control portion 109 can include a reporter portion 110 and/or a controller portion 111. These portions or components of the system 100 are schematically shown in FIG. 1. Although these portions are schematically shown as separate components, some or all of these portions can be combined into a single component. For example, although the clearer portion 112 is schematically illustrated as a separate component from the collector portion 102, in certain embodiments the collector portion 102 can be configured to perform the function of the clearer portion 112 or otherwise be integrated with the clearer portion 112, and/or with the other portions of the system 100. As such, although schematically shown as separate components or portions, reference to any of the collector portion 102, the sensing portion 104, the communication or control portion 109, and/or the clearer portion 112 in the description herein can also include reference to any of the other corresponding portions and components of the system 100. Moreover, each of these portions can be in communication with some or all of the other corresponding portions of the system 100, as schematically shown in FIG. 1. Several features of the functions of these components of the system 100 are described below with reference to FIGS. 2A and 2B. Furthermore, the system 100 illustrated in FIG. 1 may be referred to herein as a sensor or tattletale sensor.

As also described in detail below, the components of the system 100 (e.g., the collector portion 102, sensor portion 104, communication or control portion 109, and/or clearer portion 112) are configured to collect, analyze, and otherwise use miniscule fractions of a target sample interest. For example, the collector portion 102 can selectively gather or accumulate microscopic, micro-scale, molecular or even atomic sized portions of the target sample. Furthermore, the microscopic portion of the target sample is a relatively miniscule portion of the target sample itself. As such, large quantities of the target sample are not required to determine the presence of or properties of the target sample. Moreover, the sensor portion 104 can detect the presence of the target sample or otherwise analyze the molecular portions of the target sample automatically (i.e., once the collector portion 102 accumulates the portion, the sensor portion 104 can instantaneous sense the presence or properties of the portion in response to the portion being present). As such, in addition to having the capability of collecting and analyzing miniscule sample, the system 100 itself can be a microscopic or other relatively small system. Moreover, the communication or control portion 109 can provide a real-time, immediate, or otherwise instantaneous indication or report of the collection and analysis of the sample. For example, the reporter portion 110 can selectively send a signal or provide other suitable indications relating to the collection, detection, and/or analysis of the target sample. In addition, the controller portion 111 can provide for adaptive control of the sample collection, analysis, reporting, and/or clearing, as well as provide other information based on these actions, such as an indication of a trend of the collection or analysis. For example, the controller portion 111 can process or otherwise provide an indication of the amount collected or rate of collection based off of miniscule amounts of the collected and analyzed target sample portions. In certain embodiments, the controller 111 can include a processor and/or memory for storing computer readable instructions, as well as for storing information related to the collection and analysis (e.g., trends, rates, and/or quantities of sample collection, types of samples, locations of sample collection, etc.) The communication portion 109 can send information to and receive information from a remote controller, including for example, to take specific actions in response to a remote controller. In addition, the communication portion 109 can include an internal clock or external clock for indicating a rate of sampling (e.g., collecting and/or clearing) the target sample. Moreover, and as described in detail below, the system 100 can be used or arranged in a network or matrix of similar systems that can communicate with one another as well as with a central controller.

FIG. 2A is a flow diagram of a process or method 200 configured in accordance with an embodiment of the disclosure. The method 200 can be implemented, controlled, or otherwise carried out by one or more of the systems 100 described above with reference to FIG. 1. Referring to FIG. 2A, the method 200 includes collecting a portion of a target sample (block 222). As described in detail below, collecting the portion of the target sample can include collecting or accumulating a microscopic portion of the target sample, such as, for example, a molecular-sized portion of the target sample. As further described below, the collector portion 102 of FIG. 1 can collect the target sample using numerous techniques, including, for example, any of the following techniques and/or applications: specifically designed surfaces for molecular filtering, optical analysis employing indices of refraction, capillary action, thermal analysis, adsorption, absorption, adhesion collection, analysis of hydrophobic and hydrophilic properties, nano radios frequency modulation, etc. Several of these technologies that can be applied to the collector portion 102 of FIG. 1, as well as several representative environments, are described in detail below with reference to the remaining Figures.

As shown in FIG. 2A, after collecting the portion of the target sample, the method 220 further includes sensing one or more properties of the target sample (block 224). The sensing of method 220 can be performed by the sensing portion 104 of the system 100 of FIG. 1, which includes the detector portion 106 and the analyzer portion 108. For example, and as shown in FIG. 2B, which illustrates a portion of the method 220 illustrated in FIG. 2A, the sensing step (block 224) of the method 220 can optionally include sub-steps or subroutines detecting one or more properties of the target sample (block 225), as well as analyzing the one or more properties of the target sample (block 227). In certain embodiments, detecting the presence of the collected target sample or detecting a sufficient accumulated volume of the target sample may be sufficient for purposes of sensing the target sample. In other embodiments, however, it may be desirable or advantageous to analyze the portion of the target sample for a specific property or indicator. In addition, the step of sensing one or more properties of the sample may only require a miniscule or molecular sized portion of the target sample. In still further embodiments, the sensing step (block 224) of the method 220 may be dependent upon the mechanism or method used to collect the portion of the target sample (e.g., at block 222). Moreover, the sensing can include analyzing a trend indicated by the collection-rate of the target sample, or a comparative evaluation of the particular chemistry of the target sample. Several embodiments of suitable components and configurations for sensing (e.g., detecting and/or analyzing) the target sample are described in detail below.

The method 220 further includes reporting an indication of the detection and/or analysis of the portion of the target sample (block 226). The reporting step of method 220 can be performed by the reporter portion 110 of the system of FIG. 1. In certain embodiments, the reporting can include sending or transmitting a signal (e.g., via a wired or wireless medium) to a controller or another similar system indicating the presence of the detected target sample or the results of the analysis of the one or more properties of the target sample. In other embodiments, the signal can include an indication of an appropriate action in response to the sensed target sample. For example, the signal can include information regarding preventative maintenance or safety relating to the target sample, as well as information relating to the location, quantity, concentration, or other property of the target sample. Moreover, the reporting signal can be sent simultaneously or otherwise in real-time with the sensing of the target sample, or the reporting signal can be stored and transmitted at a later time. Several embodiments of suitable components and configurations for reporting the indication of the detection or analysis of the target sample are described in detail below.

The method 220 can further optionally include clearing at least a portion of the collected target sample (block 228). The clearing can be performed by the clearer portion 112 of the system 100 of FIG. 1. In certain embodiments the collected portion of the target sample can be cleared or removed to allow for additional collecting of new portions of the target sample. In other embodiments, however, the target sample may not be cleared. Several embodiments of suitable components and mechanisms for clearing the target sample are described in detail below. Moreover, according to embodiments of the disclosure, all or portions of the steps of the method 220 illustrated in FIGS. 2A and 2B can be cyclically repeated, as indicated by arrow 229, for continuous or automatic collection, analysis, reporting, and/or clearing. As described below, embodiments of the present disclosure include unique features that enable the collection and analysis of microscopic target samples for real-time reporting and adaptive control.

B. Embodiments and Features of Architectural Constructs that can be Used for the Collector, Sensor, Reporter, and/or Clearer Portions of a System As described above with reference to FIGS. 1-2B, the collector portion 102 is configured to gather, accumulate, attract, or otherwise collect portions of a target sample. According to certain embodiments of the disclosure, the collector portion 102 can be at least partially made from an architectural construct as disclosed in U.S. Patent Application 61/523,199, entitled "ARCHITECTURAL CONSTRUCT HAVING FOR EXAMPLE A PLURALITY OF ARCHITECTURAL CRYSTALS," filed concurrently herewith. For example, the architectural construct can be composed of a synthetic matrix characterization of crystals that can be specifically designed to achieve desired (1) thermal properties, (2) electromagnetic, optical, and acoustical properties, (3) catalytic properties, (4) capillary properties, and (5) sorptive properties. The architectural construct can be designed to utilize some or all of these properties for a particular application, such as collecting a predetermined target sample. The architectural construct's behavior depends on its composition, surface structures located on its layers, it layer orientation, its dopants, and the coatings (including catalysts) that are applied to its surfaces. When it is configured as layers, its behavior also depends on the thicknesses of its layers, spacers between its layers, the distances separating its layers, and the means used for supporting its layers and/or separating its layers. An architectural construct is a macro-structure designed to facilitate micro-processing on a nano-scale. From a macroscopic standpoint, it can be configured to have a specific density, modulus of elasticity, and/or section modulus. And it can be designed so that from a microscopic standpoint it acts as a molecular processor, charge processor, and/or bio processor.

The collector portion 102 at least partially composted of an architectural construct for collecting a portion of a target sample can be configured in many ways. For example, a designer can arrange it as a solid mass (e.g., as multiple single-atom-thick layers stacked upon each other), as multiple spaced apart layers that are individually as thin as an atom, or in another configuration through which it will exhibit a desirable property. A designer can also dope the architectural construct or coat its surfaces with a substance, each of which causes it to behave in a different way than it would have otherwise. Illustratively, FIG. 3A is a molecular diagram of a layer of a matrix characterization of crystals 330a of an architectural construct. The layer 330a may include carbon, boron nitride, or another suitable substance. For example, the matrix characterization of crystals 100 may be a layer of graphene. A layer of a matrix characterization of crystals like that shown in FIG. 1A can be configured as an architectural construct by specializing the layer, such as by doping the layer or arranging the layer with other layers in a particular configuration so that the resulting construct exhibits a particular property. Layers 330a of a matrix characterization of crystals that form an architectural construct can be configured stacked together as a layer that is thicker than an atom (e.g., graphene stacked to form graphite) and/or spaced apart from each other by particular distances. Furthermore, layers of an architectural construct can be oriented with respect to each other in various ways.

Figure 3B:
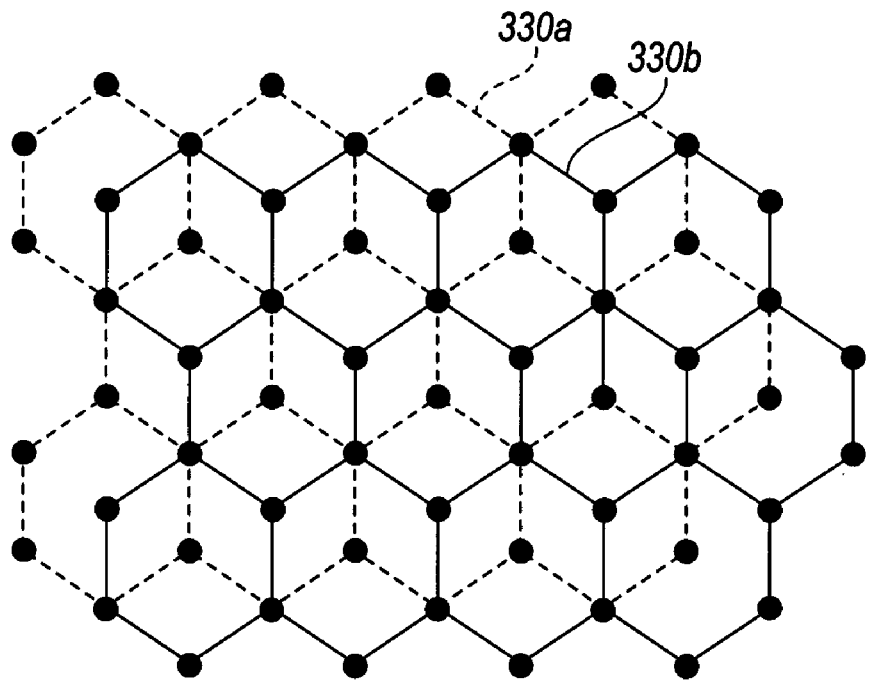

FIG. 3B is a schematic molecular diagram of an architectural construct including a second layer 330b of a matrix characterization of crystals stacked on the first layer 330a of a matrix characterization of crystals of FIG. 3A (the first layer 330a is shown in broken lines in FIG. 3B). Referring to FIGS. 3A and 3B together, the layers consists of graphene, which is an atom-thick planar sheet of carbon. In some implementations, a single atom-thick sheet of a matrix characterization of crystals is made of another substance besides carbon, like boron nitride. In still further embodiments, the architectural construct may be configured as a solid mass. A solid mass architectural construct can consist of, for example, graphite or boron nitride. An architectural construct configured as a solid mass includes multiple single-atom-thick layers stacked together. An architectural construct configured as a solid mass is specialized, meaning it has been altered to behave in a specific way or to perform a predetermined function. In some implementations, a solid mass is specialized by doping or by orienting its single-atom thick layers a particular way with respect to one another.

In some implementations, first and second layers of an architectural construct are configured so that atoms of the first layer and atoms of the second layer vertically aligned when viewed from above. For example, the molecules of an architectural construct consisting of two layers that are aligned in this manner will appear like the first layer 330a of the architectural construct from FIG. 3A when viewed from above. In other embodiments a first layer can be rotated relative to a second layer by 30-degrees. In some implementations, a first layer of an architectural construct includes a first substance, such as carbon, and a second layer of the construct includes a second substance, such as boron nitride. Layers composed of or doped with different substances may not appear planar as larger molecules warp the planar surface. As further detailed below, some properties of an architectural construct are influenced by the orientation of its layers relative to each other. For example, a designer can rotate or shift a first layer of a construct relative to a second layer of the construct so that the construct exhibits particular optical properties, including a specific optical grating Moreover, the layers of the architectural construct can be oriented in a position with respect to each other (i.e., offset and/or rotated as discussed above with respect to FIGS. 1A-C) by applying trace crystal modifiers, such as neon, argon, or helium, at the time of a layer's deposition, through a heat treat that moves the molecules to a particular orientation, or through torque of the crystal during exfoliation.

An architectural construct configured in accordance with embodiments of the disclosure can be composed of a single substance (e.g., graphene, boron nitride, etc.) or it can be specialized by being doped or reacted with other substances. For example, an architectural construct consisting of graphene may have areas that are reacted with boron to form both stoichiometric and non-stoichiometric subsets. The graphene can be further specialized with nitrogen and can consist of both graphene and boron nitride graphene with a nitrogen interface. In some implementations, compounds are built upon the architectural construct. For example, from a boron nitride interface, a designer can build magnesium-aluminum-boron compounds. By specializing an architectural construct in these ways, a designer can create a construct that exhibits different properties than a construct composed of only one substance would.

Figure 3C:
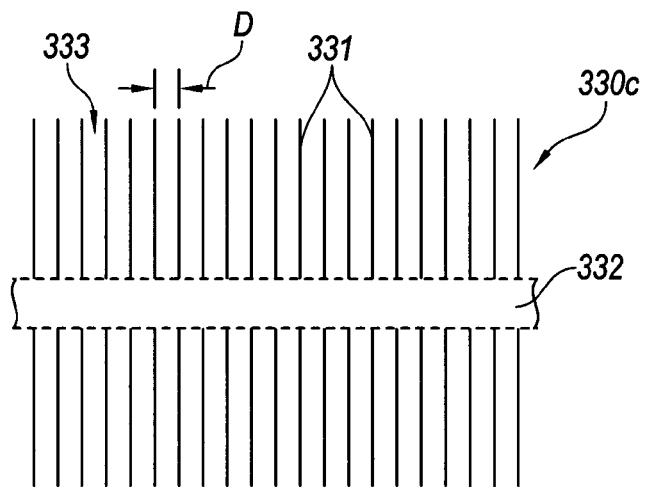
FIGS. 3C-3E and 3G are cross-sectional side views and FIG. 3F is an isometric cross-sectional view of corresponding architectural constructs configured with parallel and spaced apart layers in accordance with embodiments of the disclosure.

Architectural constructs including parallel layers spaced apart from one another are capable of yielding a wide range of properties and achieving many outcomes. For example, FIG. 3C is a cross-sectional side view of an architectural construct 330c configured as parallel and spaced apart layers 331 that can be comprised of any of a number of substances, such as graphene, graphite, or boron nitride. The parallel layers 331 may be rectangular, circular, or other suitable shapes. In FIG. 3C, the layers 331 include an opening or hole through which a support tube 332 supports the architectural construct 330c. The layers 331 are each separated by a distance D creating zones 333 between the layers 331. The individual layers 331 of the architectural construct 330c can be made to have any suitable thickness. In FIG. 3C, for example, each of the parallel layers 331 can be a single atom thick. For example, each layer may be a sheet of graphene. In some implementations, the layers of the architectural construct are thicker than one atom. In still other embodiments, the layers 331 can have different thicknesses, as well as be spaced apart by different distances.

Figure 3D:
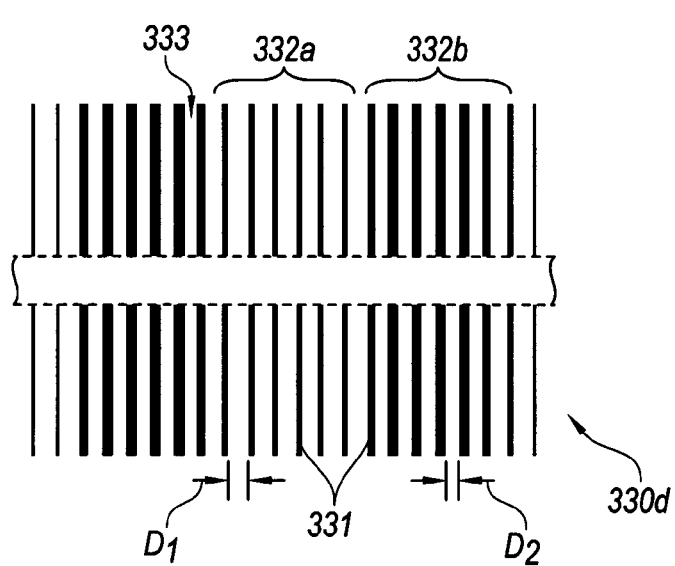
Figure 3E:
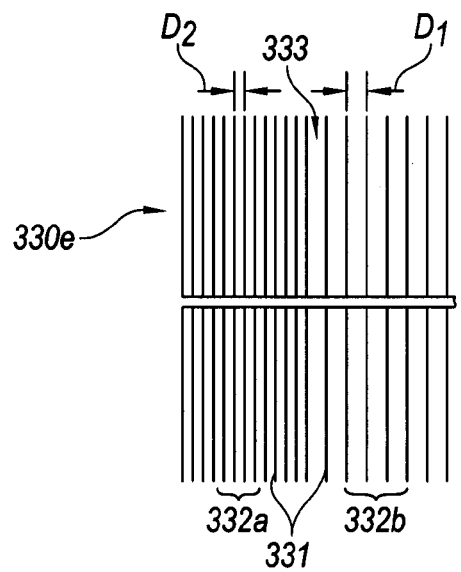

FIG. 3D, for example, is a cross-sectional side view of an architectural construct 330d with multiple layers 331 of different thicknesses or widths. In certain embodiments, the layers 331 are each thicker than one atom. In other embodiments, however, some of the layers 331 may be only a few atoms thick and other layers 331 may be much thicker, such as 20 atoms or more. More specifically, the layers 331 can include a first group 332a of relatively thin layers 331, and a second group 332b of relatively thicker layers 331. According to additional features of the illustrated embodiment, the first group 332a of layers 331 can include a first distance $D_1$ between adjacent layers 331 that is greater than a second distance $D_2$ between adjacent layers 331 of the second group 332b. These spacing distances accordingly create zones 333 between adjacent layers 331. FIG. 3E is a cross-sectional side view of an architectural construct 330e with multiple layers 331 having approximately the same thickness but that are spaced apart from one another by varying distances. For example, a first group 332a of layers 331 can be spaced apart from each other by a first distance D1 that is less than a second distance D2 spacing apart corresponding layers 331 of a second group 332b. FIG. 3E also illustrates the zones 333 between the adjacent layers 331. The zones 333 are sized according to the spacing distances between the layers 331, therefore creating, for example, larger zones 222 in the second group 332*b* than in the first group 332*a*.

Figure 3F:
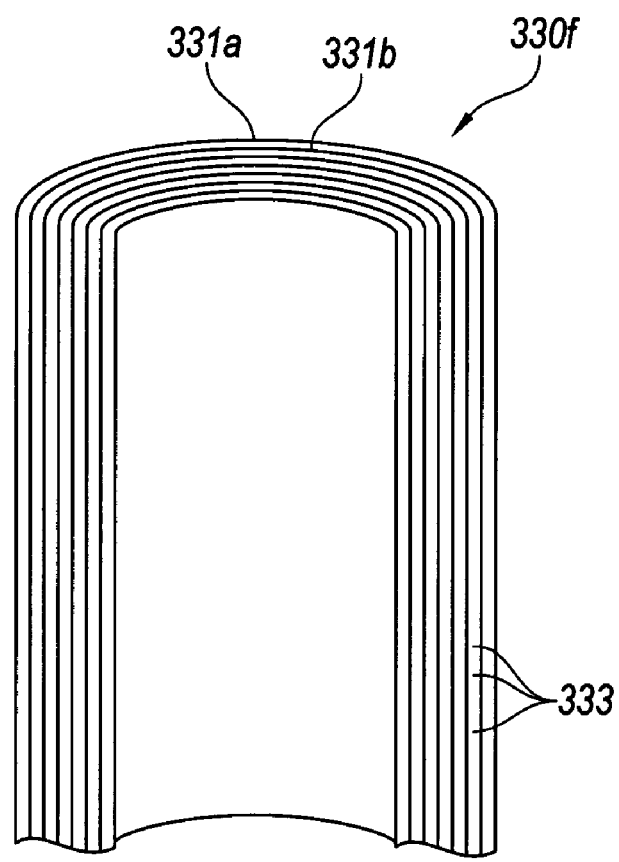

FIG. 3F is a cross-sectional isometric partial view of an architectural construct 350*f* consisting of concentric tubular layers 331 of a matrix characterization of crystals. For example, a first layer 331*a* of the architectural construct 330*f* is tubular and has a greater diameter than an adjacent second layer 331*b*. The architectural construct 350*f* can include multiple concentric layers spaced apart in this manner.

Figure 3G:
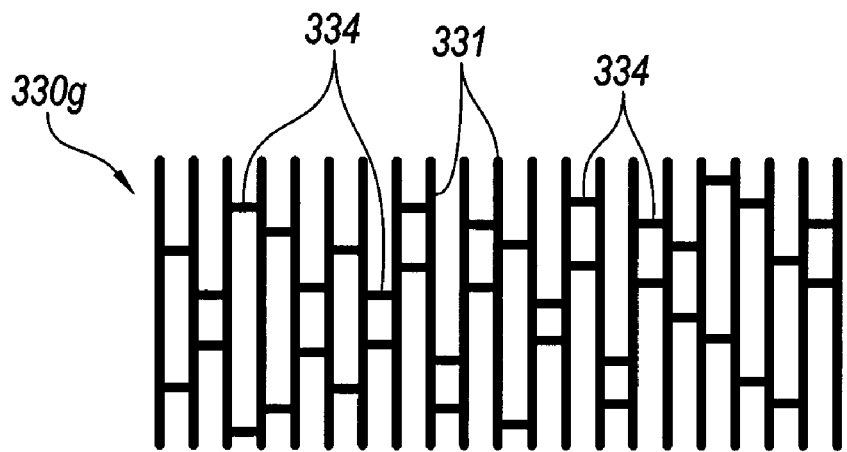

Turning next to FIG. 3G, FIG. 3G is a side cross-sectional partial side view of an architectural construct 330*g* illustrating several spacers 334 between adjacent layers 331. In certain embodiments, the spacers can be composed of titanium (e.g., to form titanium carbide with a graphene layer), iron (e.g., to form iron carbide with a graphene layer), boron, nitrogen, etc. To form the configuration shown in FIG. 3G, in some implementations a gas is dehydrogenated on the surface of each layer 331, thereby creating the spacers 334 where each molecule is dehydrogenated. For example, after a layer 331 of the architectural construct 330*g* is exfoliated, methane may be heated on the surface of the layer 331, which causes the methane molecules to split and deposit carbon atoms on the surface of the layer 331. The larger the molecule that is dehydrogenated, the larger the spacing or spacer 334 that is created. For example, propane, which has three carbon atoms per molecule, will create a larger spacer 334 than methane, which has one carbon atom per molecule. In some implementations, the spacers 334 are surface structures, like nanotubes and nanoscrolls, which transfer heat and facilitate in the loading of substances into the architectural construct the 330*g*. Architectural constructs that include these types of surface structures are described U.S. patent application Ser. No. 12/857,515, which is incorporated herein by reference in its entirety.

An architectural construct including any of the configurations described above can be formed in a variety of ways, as described in detail in U.S. Patent Application 61/523,199, entitled "ARCHITECTURAL CONSTRUCT HAVING FOR EXAMPLE A PLURALITY OF ARCHITECTURAL CRYSTALS," filed concurrently herewith, as well as in U.S. Pat. No. 6,503,584 and pending U.S. patent application Ser. No. 12/857,515, each of which is incorporated herein by reference in its entirety. These methods can include, for example, forming layers or an architectural construct by dehydrogenating a gas (e.g., a hydrocarbon) within a frame to form the first layer, and to dehydrogenate a substance (e.g., titanium hydride) to form spacers on the inside surface of the layer before dehydrogenating the gas to form the second layer on the spacers or surface structures. Subsequent layers can then be deposited in a similar fashion. Other methods can include machining a single crystal into a desired shape and exfoliating the single crystal into layers. Further approaches can include diffusing a fluid (e.g., hydrogen) into a crystal and exfoliating layers from the crystal. These layers can be exfoliated a predetermined distance away from an adjacent layer. Moreover, spacers or surface structures can also be deposited between the layers.

Several features of the architectural constructs as disclosed herein and in U U.S. Patent Application 61/523,199, entitled "ARCHITECTURAL CONSTRUCT HAVING FOR EXAMPLE A PLURALITY OF ARCHITECTURAL CRYSTALS," filed concurrently herewith, filed concurrently herewith and incorporated by reference herein in its entirety, can be specifically designed to implement the collecting, sensing, reporting, and/or clearing features of the system 100 as described above with reference to FIG. 1. For example, an architectural construct can be designed so that it has a specific density, modulus of elasticity, and section modulus. These macroscopic characteristics affect the properties that an architectural construct exhibits at the microscopic level. More specifically, an architectural construct's density is defined as its mass per unit volume, which can be affected by a number of different parameters. One parameter is the composition of the matrix characterization of crystal. For example, a crystal of boron nitride generally has a higher density than a crystal of graphite. Another parameter is the distance separating the layers of an architectural construct. Increasing or decreasing the spacing between the layers will correspondingly increase or reduce an architectural construct's density. An architectural construct's density will also be greater in embodiments in which its layers are spaced apart by spacers relative to embodiments in which the layers are similarly spaced but not by spacers. Dopants that are added to an architectural construct will also affect the density (e.g., the greater the amount of dopants, the greater the corresponding density).

Another property of an architectural construct that can be specifically designed is the modulus of elasticity, which is its tendency to be deformed elastically when a force is applied to it (e.g., defined as the slope of its stress-strain curve in the elastic deformation region). Like its density, an architectural construct's modulus of elasticity depends in part on the thicknesses of its layers, their spacing, and their composition. Its modulus of elasticity will also depend on how the layers are fixed relative to one another. For example, if the layers are supported by a central tube or support, the individual layers can generally elastically deform by a greater amount than if they are fixed relative to one another using spacers. When spacers fix two layers relative to one another, each layer will reinforce the other corresponding layer when pressure is exerted on either layer, thereby dampening the deflection that results from a given force. The amount that each layer reinforces each other is contingent, in part, on the concentration of spacers between the layers and how rigidly the spacers hold the layers together.

An additional property of an architectural construct that can be specifically designed is the section modulus, which is the strength of the architectural construct or ratio of a cross section's second moment of area to the distance of the extreme compressive fiber from the neutral axis. An architectural construct's section modulus will depend on the size and shape of each layer of architectural construct. An architectural construct's density, modulus of elasticity, and section modulus, as well as other macroscopic properties, can be constant throughout the architectural construct or they can vary by section or cyclically. Just as an architectural construct's density, modulus of elasticity, or section modulus can affect the properties that are exhibited by the architectural construct, varying these macroscopic characteristics either by section or cyclically can cause the architectural construct to behave differently at different parts or sections of the construct. For example, by separating an architectural construct's layers in a first section by a greater amount than in a second section (thereby giving it a greater density in the second section than in the first), the architectural construct can be made to preferentially load, collect, or otherwise accumulate a first substance in the first section and a second substance in the second section.

C. Embodiments and Features of Collector Portions of a System

As described above with reference to FIG. 1, the collector portion 102 of the system 100 is configured to load, accumulate, or otherwise collect portions (e.g. microscopic or molecular portions) of a target sample. The collector portion 102 can be at least partially composed of an architectural construct as described in detail above. As further described in detail below, the collector portion 102 can collect portions of a target sample through various mechanisms and or methods.

1. Features Relating to Loading and Unloading of Collector Portions

In certain embodiments the collector portion 102 can be configured as a selective surface that can selectively load or accumulate portions of a predetermined target sample. More specifically, in certain embodiments where the collector portion is an architectural construct with multiple spaced apart layers, the layers can be configured to load a target substance into zones between the layers. A molecule of a target substance is loaded between parallel layers when it is adsorbed onto the surface of a layer or absorbed into the zones between the layers. For example, referring back to FIG. 3C, the architectural construct 300c may load molecules of a substance presented through the support tube 332 to an inner periphery of the layers 331 into the zones 333. For example, the support tube 332 may supply the target substance to the zones 333 through perforations in the support tube 332.

In some implementations, the architectural construct is configured to selectively load a particular molecule or molecules and avoid other molecules of non-target substances (e.g., by loading a first target molecule and refraining from loading a second non-target molecule). For example, a first of set layers may be configured so that they are a particular distance apart that facilitates the selective loading of a first molecule and not a second molecule. Similarly, a second set of layers may be configured so that they are a particular distance apart to facilitate the loading of a third molecule but not the second molecule. Surface tension at edges of the layers will also affect whether a molecule is loaded into an architectural construct. For example, if the first set of layers has already loaded molecules of a first substance, surface tension at the inside edges of the first set where molecules of the substance are loaded from may prevent the first set of layers from loading molecules of the second substance but allow the first set of layers to continue load molecules of the first substance.

In some implementations, an architectural construct is configured to be non-sacrificial. For example, a non-sacrificial construct can load and unload substances or perform other tasks without sacrificing any of its structure. In other implementations, an architectural construct is configured to sacrifice atoms from its crystalline structure to facilitate a particular result. For example, an architectural construct that is composed of boron nitride may be configured to load desired target sample, and which the boron nitride may react with. As a result, atoms from the construct will be sacrificed in the reaction of the boron nitride with the target sample, and when the product is unloaded from the construct, the architectural construct will have lost the sacrificed molecules of boron nitride. In some implementations, a construct that has sacrificed its structure can be at least partially restored. For example, an architectural construct consisting of boron nitride can be restored by presenting the construct with new boron nitride molecules and applying heat. The new boron nitride molecules may self-organize into the original shape of the architectural construct.

As such, embodiments disclosed herein can selectively collect specific constituents of a target sample to utilize chromatography principles to analyze the collected or separated constituents of the target sample.

2. Features Relating to Thermal Properties that Affect Collector Portions

One of the factors that affects whether and how a collector portion configured as an architectural construct will load portions of a target substance include the thermal properties of the collector portion. In some implementations, the architectural construct is configured to transfer heat away from the zones where a molecule is loaded into or from. When an architectural construct is cooled, it may load molecules faster or it may load molecules than it was to load when it was hotter. Similarly, an architectural construct may be unloaded by transferring heat to the architectural construct. In still further embodiments, the amount of heat that is absorbed, reflected, or insulated can be the property that is "collected" from the target sample and used for further analysis. Further details of the thermal properties and capabilities of a collector portion of a system that is configured as an architectural construct are described in detail below for collecting thermal and/or radiant energy.

In certain embodiments, the architectural construct can be configured to collect heat or energy, which can later be used to determine one or more properties of the target sample. For example, an architectural construct can be configured to have specific thermal properties that affect heat conduction and absorption. Even when its crystalline layers readily conduct heat, an architectural construct can be configured to have either a high or low availability for conductively transferring heat. It can also be configured so that radiative heat is transmitted through passageways or elsewhere within the construct, reflected away from the construct, or absorbed by the construct. This section describes various implementations of architectural constructs that are designed to have specific thermal behaviors. Some crystalline substances, like graphene, graphite, and boron nitride, readily conduct heat. In some applications, an architectural construct composed of one of these substances is configured to transfer heat between two locations or away from or two a particular location. In other applications, the architectural construct is configured so that heat may be efficiently transferred into and out of the construct as needed. An architectural construct composed of a substance like graphene can be rapidly heated or cooled. Despite having a much lower density than metal, an architectural construct can conductively transfer a greater amount of heat per unit area than solid silver, raw graphite, copper, or aluminum.

A one-atom-thick graphene layer is seemingly mostly open space between defining carbon atoms. However, graphene provides extremely high thermal and electrical conductivity in directions within the plane of atoms but only about 2.3% of white light that strikes it is absorbed. Similarly about 2% to 5% of the thermal energy spectrum radiated orthogonally at the place of atoms is absorbed while radiative heat rays parallel to separated architectural construct layers can be transmitted with even less attenuation. The net amount of light that an architectural construct absorbs depends in part on the orientation of successive layers relative to one another. Variations in the orientations of layers of an architectural construct, as discussed above, can enable various new applications. For example, radiative energy can be delivered to sub-surface locations via more absorptive orientations, such as the orientation shown in FIG. 3B. As another example, radiation can be polarized via other suitable orientations, and these orientations can be further modified by offsetting a layer in the direction of its plane by a certain amount, such as described above with respect to FIGS. 3A and 3B.

In certain embodiments, an architectural construct can be arranged to have a high availability for conductively transferring heat by configuring the architectural construct so it has a high concentration of thermally conductive pathways through a given cross section of the construct. An architectural construct can be arranged to have a low availability for conductively transferring heat by configuring the construct so it has a low concentration of thermally conductive pathways through a given cross section of the construct. For example, in embodiments having a first group of layers of an architectural construct that are an atom thick and are spaced a first distance away from one another, and a second group of layers are an atom thick and are spaced a second distance away from one another that is greater than the first distance, the first group of layers has a higher concentration of thermal passageways than over the span of the second group of layers (assuming that the groups of layers span approximately the same distance). Accordingly, the first group of layers can have a higher availability for conductively transferring heat than the second set. It also follows that the second group does a better job than the first group at thermally insulating an object located or target sample. Moreover, in some implementations an architectural construct can be configured as parallel layers that are arranged to insulate a surface that the layers are not orthogonal to. For example, the architectural construct can be configured so its layers contact a flat surface at 45-degrees by offsetting the edges of consecutive layers by a particular amount so that the layers achieve this angle with the surface when placed against it. In some implementations, an architectural construct is arranged to have a higher availability for conductively transferring heat by configuring it having thicker layers.

Architectural constructs can further bon configured to collect or accumulate radiant energy. An architectural construct configured in accordance with embodiments of the disclosure can be arranged to reflect, refract, or otherwise transform radiant energy. Accordingly, an architectural construct may be configured to interact in a specific way with radiant heat. In some implementations, an architectural construct is configured to transmit radiant heat through passageways within the construct. This transfer of radiant heat can be at the speed of light. For example, the spacing between layers may be a particular distance, and the individual layers may be configured a particular thickness so that incident infrared energy that is parallel to the layers enters and is transmitted through zones between the layers. More specifically, these distances and thickness can be configured to collect or transmit radiant energy of specific wavelengths. For example, to transmit radiant energy of a particular frequency, an architectural construct can be comprised of layers of boron nitride that are spaced apart according to quantum mechanics relationships. Similarly, as previously noted, an architectural construct can also be configured to specifically absorb radiant energy. For example, the layers of the first set of layer may be spaced apart a particular distance, be composed of a particular substance, and be a particular thickness so that at least a portion of incident infrared energy is absorbed by the layers. Opacity of each individual layer or of a suspended layer is 2.3% of the orthogonal radiation as established by quantum electrodynamics. Opacity of a group of layers depends upon their spacing, orientations of the architectural construct's layers, and the interactions of relativistic electrons within the layers and the selection of spacers, such as the surface structures.

A collecting portion that is composed of an architectural construct can also be arranged to shield or insulate an object from radiative energy, including radiant heat. In some implementations, an architectural construct insulates an object from radiant heat by reflecting the radiant energy or by transmitting the radiant energy through passageways around or away from the object. Moreover, an architectural construct's thermal properties can also be changed by adding a coating to surfaces of the construct or by doping the construct. For example, the architectural construct 400 can be doped as it is self-organized or by diffusion or ion implantation to increase its thermal conductivity generally or in specific areas or directions. It can be coated with metals, such as aluminum, silver, gold, or copper, to reflect more radiant heat than it would have otherwise.

3. Features Relating to Acoustic, Electromagnetic, and Optical Properties that Affect the Collector Portion Additional factors that affect whether and how a collector portion configured as an architectural construct will collect portions of a target substance include the acoustical, electromagnetic, and optical properties of the collector portion. In certain embodiments, for example, architectural constructs can be made to exhibit specific properties in response to acoustic energy. For example, they can be configured to acoustically and/or electromagnetically resonate at specific frequencies. They can also be constructed to have a particular index of refraction, and they can be designed to shift the frequency of incident electromagnetic waves. These properties can be controlled by arranging a construct to have a particular configuration, including a specific density, modulus of elasticity, and section modulus. As discussed above, these parameters can be adjusted by changing the composition of an architectural construct, its treatment, and its design. Moreover, the layers of the architectural construct can be composed of graphite to have an index of refraction that is adjusted by the spacing between layers and/or by the addition of adsorbed and/or absorbed substances within the spacings. Additionally, in some implementations, dopants are added to an architectural construct to change its index of refraction. For example, layers of an architectural construct comprised of boron nitride may be doped with nitrogen to increase its index of refraction An architectural construct's acoustic resonance frequency changes with a number of factors. A dense architectural construct will resonate at a lower frequency than one that is less dense and otherwise identical. Accordingly, when an architectural construct is configured as parallel layers, a thin layer will have a higher resonant frequency than a thicker layer. Moreover, less densely packed layers (e.g., greater distances between layers) will also have a higher resonant frequency than more densely packed layers. An architectural construct supported firmly on its edges will resonate at a lower frequency than one that is supported at its center. Additionally, an architectural construct with a high modulus of elasticity will resonate at a greater frequency than one with a low modulus of elasticity, and an architectural construct with a high section modulus will resonate at a lower frequency than an architectural construct with a smaller section modulus. Moreover, the resonance frequency of any of the layers can be reduced by making the diameter of the layers larger. In some implementations, all of the layers of an architectural construct are designed to resonate at the same frequency, however in other embodiments portions of the architectural construct will resonate at different frequencies. An architectural construct's resonant frequency will also depend on its composition. Additionally, in some implementations, dopants and/or coating can be added to an architectural construct to increase or reduce its acoustic resonance frequency. An architectural construct's resonance frequency can also be reduced by adding spacers between the layers.

In certain embodiments, an architectural construct can also be configured to resonate electromagnetically at a particular frequency. For example, its density, modulus of elasticity, and section modulus can be chosen for each layer so that the construct or each layer has a particular resonance frequency in response to an applied electromagnetic force. An architectural construct may also be configured to absorb radiant energy that is a particular wavelength.

In some implementations, an architectural construct is configured to load molecules at a faster rate or at a higher density when an electric charge is applied to the construct. For example, graphene, graphite, and boron nitride are electrically conductive. An architectural construct composed of these materials may be configured to load molecules at a higher rate when an electric charge is applied to its layers. Implementations for heating or cooling an architectural construct and for applying an electric charge are disclosed in U.S. patent application Ser. No. 12/857,515, which is incorporated herein in its entirety by reference. In some implementations, an architectural construct is configured to load or unload a substance when radiant energy is directed at the construct. For example, the distance between each of the parallel layers may be selected so that the architectural construct absorbs infrared waves, causing the layers to heat up and unload molecules of a substance that it has loaded. As Moreover, in some implementations a catalyst can be applied to the outside edges of the layers to facilitate the loading of substances into the zones between the layers.

In addition, in some implementations the layers of an architectural construct are spaced apart to polarize incident electromagnetic waves. Also, as discussed above, an architectural construct can be configured to insulate an object from radiation. In some implementations, an architectural construct insulates an object from radiation by reflecting the radiant energy. For example, the architectural construct can be configured to insulate an object placed on the right side of the architectural construct from radiation on the left side of the construct. For example, each layer can be composed of boron nitride, and be spaced apart to reflect electromagnetic radiation within specified wavelengths.

4. Features Relating to Selective Surfaces and Wavelength Shifting Properties that Affect the Collector Portion Additional factors that affect whether and how a collector portion configured as an architectural construct will collect portions of a target substance include the selective surface and wavelength shifting properties of the collector portion. In certain embodiments, for example, a collector portion configured as an architectural construct can include a surface that is positioned and/or configured to enhance radiation entry into the collector portion or other desired zones by (1) passing a portion of the radiation having a selected orientation and/or wavelength and (2) re-radiating a portion of the energy at a different wavelength. A number of factors influence whether an architectural construct will absorb radiant energy that is a particular wavelength. For example, the ability of the architectural construct to absorb radiant energy that is a particular wavelength depends on the layers' thicknesses, their spacing, their composition, their dopants, their coatings, and/or spacers positioned between the layers. In some implementations, an architectural construct is configured to transmit radiant energy that is a first wavelength and absorb and reradiate energy that is a different wavelength from the received radiant energy. For example, the architectural construct may be configured so that the layers are parallel to some but not all incident radiant energy. The parallel layers can be configured to transmit radiant energy that is parallel to the layers through the construct and absorb non-parallel radiation. In some implementations, a re-radiative substance (e.g., silicon carbide, silicon boride, carbon boride, etc.) is coated on the surfaces of the architectural construct, such as by spraying the architectural construct with the substance. Then, when non-parallel radiation contacts the architectural construct, the re-radiative substance absorbs the non-parallel radiation and reradiates the energy at a different wavelength than the energy was received at.

An architectural construct can also be configured to have a particular index of refraction (i.e., an index of refraction within a particular range or an exact value). An architectural construct's index of refraction is a function of, among other variables, the composition of the layers (e.g., boron nitride, graphite, etc.), the thicknesses of the layers, dopants, spacers, and the distances that separate the layers. For example, the distance between the parallel layers and the thicknesses of the layers, may be selected so that the parallel layers have a particular index of refraction. Additionally, in some implementations, dopants are added to an architectural construct to change its index of refraction. For example, layers of an architectural construct comprised of boron nitride may be doped with nitrogen to increase its index of refraction. An architectural construct's index of refraction may change when a substance is loaded into the architectural construct. For example, an architectural construct existing in a vacuum may have a different index of refraction than when hydrogen is loaded into the construct and expressed as epitaxial layers and/or as capillary between the epitaxial layers. In some implementations, the index of refraction of a first portion of an architectural construct is different from the index of refraction of a second portion of the architectural construct. For example, a first set of the parallel layers may have a different index of refraction than a second set of layers because the first set of layers are thinner and are spaced apart by a greater distance than the layers in the second set of layers.

Figure 4A:
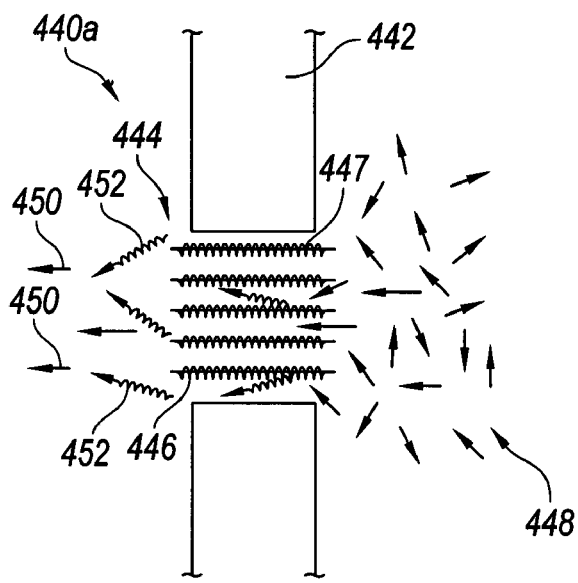
FIGS. 4A-4C are schematic cross-sectional side views of portions of a system configured in accordance with embodiments of the disclosure.
Figure 4B:
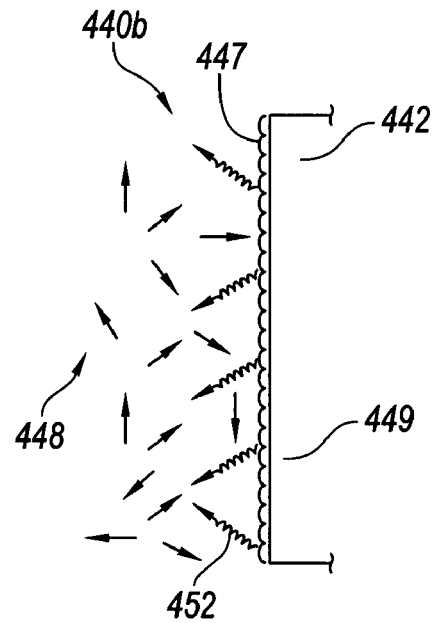
Figure 4C:
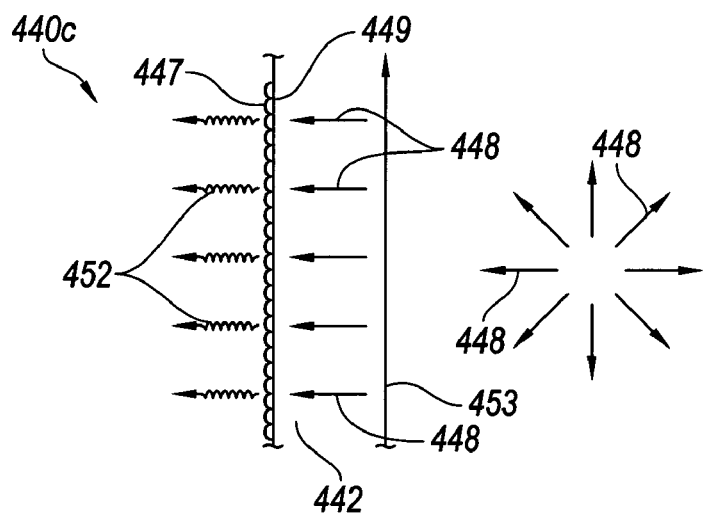

FIGS. 4A-4C illustrate several of the properties of the collector portion configured as an architectural construct to selectively transmit, absorb, and/or re-reradiate energy at different wavelengths. FIG. 4A, for example, is a schematic diagram of a portion of a system 440*a* including a collector portion having a body 442 configured as an architectural construct having a radiant energy transmissive section 444. The transmissive section 444 includes multiple spaced apart layers 446, which can include any of the properties disclosed herein with reference to the parallel and spaced apart layers of an architectural construct. In the illustrated embodiment, radiant energy indicated by arrows 448 that is transmitted generally parallel to the layers 446 can be transmitted or otherwise allowed to pass through the body 442. Radiant energy that passes through the layers 446 is indicated by arrows 450. The body 442 can absorb the radiant energy that is not transmitted through the layers 446 (e.g., non-parallel radiant energy 448 with reference to the layers 446).

According to additional features of the illustrated embodiment, individual layers 446 can include a coating 447 (e.g., silicon carbide, silicon boride, carbon boride, phosphorescent, fluorescent, etc.) for re-radiating energy that passes through the transmissive section 444. For example, radiant energy 448 that enters the transmissive section and reflects off the coating 447 can be reflected or shifted to a wavelength that is different than the entering radiant energy. For example, radiant energy that passes through the transmissive section with a different or modified wavelength are indicated by arrows 452. Accordingly, the embodiment illustrated in FIG. 4A and described above is able to enhance radiation that passes through the body 442 by (1) passing a portion of radiation 448 having a selected orientation (e.g., as represented by arrows 450 exiting the body 442), and (2) re-radiating a second portion of the radiation at a different wavelength (e.g., as represented by arrows 452 exiting the body 442).

FIG. 4B is a schematic diagram of a portion of a system 440b including a collector portion having a body 442 configured as an architectural construct having a radiant energy reflective and absorbent surface 449. The surface 449 can be configured to absorb radiant energy 448 at a particular orientation (e.g., generally transverse to the surface 449) and/or wavelength, as well as to reflect radiant energy 448 as indicated by reflected energy at arrows 452. In certain embodiments, the surface 449 can include a coating (e.g., silicon carbide, silicon boride, carbon boride, phosphorescent, fluorescent, etc.) for re-radiating energy 452. For example, the coating 447 can be configured to re-radiate the energy 452 a wavelength that is different than the wavelength that is incident to the surface 449. Accordingly, the embodiment illustrated in FIG. 4B is able to (1) absorb radiation (e.g., radiation at a predetermined orientation and/or wavelength), and (2) re-radiating a second portion of the radiation at a different wavelength (e.g., as represented by arrows 452 exiting the body 442).

FIG. 4C is a schematic diagram of a portion of a system 440c including a collector portion having a body 442 configured as an architectural construct having conductive and re-radiative properties. For example, the body 444 can be made from an at least partially conductive material (e.g., copper, beryllium oxide, etc.) and includes a first surface 453 opposite a second surface 449. The first surface 453 faces radiant energy represented by arrows 448. The body 444 is configured such that it is conductive to the radiant energy 448. As the energy 448 reaches the second side 449, the second side 449 can re-emit the radiation away from the second side 449. In certain embodiments, the second surface 449 can include a coating 447 that re-radiates the energy at a different wavelength. For example, re-radiated energy represented by arrows 452 can be re-emitted or re-radiated at a second wavelength that is different from the wavelength of the radiant energy 448.

The wavelength shifting and absorbing, transmitting, reflecting, and/or re-radiating features described above with reference to FIGS. 4A-4C can include any of the features and components as described in U.S. patent application Ser. No. 13/027,015, entitled "CHEMICAL REACTORS WITH RE-RADIATING SURFACES AND ASSOCIATED SYSTEMS AND METHODS," filed concurrently herewith and incorporated herein by reference in its entirety.

As described in detail below, the absorbed, transmitted, reflected, conducted, and/or re-radiated energy can be used to determine the presence of a target sample (i.e., the radiant energy source) and/or one or more properties or characteristics relating to the target sample (i.e., the radiant energy). For example, in certain embodiments the radiant energy can be visible light of a first color emitted from a target sample, and the re-radiated energy can be visible light of a second color different than the first color and indicative of the presence and/or properties of the target sample. Moreover, the portions of the radiant energy that are transmitted, absorbed, reflected, and/or re-radiated can be constituents that are removed or otherwise separated from the target sample.

5. Features Relating to Catalytic Properties that Affect the Collector Portion

Additional factors that affect whether and how a collector portion configured as an architectural construct will collect or load portions of a target substance include the catalytic properties of the collector portion. For example, an architectural construct can be configured to catalyze a reaction in a variety of ways that can enhance collection or loading a portion of the target sample. More specifically, an architectural construct consisting of parallel layers may catalyze a chemical reaction or a biological reaction at an edge of its layers by controlling the temperature of the reaction, by having a particular configuration of the layers that catalyzes the reaction, or by supplying a substance that catalyzes the reaction. An architectural construct can also catalyze a reaction by increasing the reaction rate, prolonging the reaction, enabling the reaction, or by otherwise facilitating the reaction. A number of variables can be changed to catalyze a particular reaction. In some implementations, for example, the thickness of the individual layers of an architectural construct are selected to catalyze a reaction. Moreover, the distances between layers and/or the layers' compositions (e.g., boron nitride, carbon, etc.) can be selected to catalyze a reaction. In additional embodiments, dopants can be added to an architectural construct, or spacers of a particular chemistry can added between layers, to catalyze a particular reaction.

The parallel layers can catalyze a reaction by transferring heat to a zone where the reaction is to occur. In other implementations, the parallel layers catalyze a reaction by transferring heat away from a zone where a reaction is to occur. For example, heat may be conductively transferred into the parallel layers (e.g., as discussed in U.S. patent application Ser. No. 12/857,515, which is incorporated in its entirety) to supply heat to an endothermic reaction within a support tube of the layers. In some implementations, the parallel layers catalyze a reaction by removing a product of the reaction from the zone where the reaction is to occur. For example, the parallel layers may absorb alcohol from a biochemical reaction within the central support tube in which alcohol is a byproduct, thereby expelling the alcohol on outer edges of the parallel layers, and prolonging the life of a microbe involved in the biochemical reaction.

In some implementations, a first set of parallel layers can be configured to catalyze a reaction and a second set of the parallel layers is configured to absorb and/or adsorb a product of the reaction. For example, a first set of layers may be configured to catalyze a chemical reaction by enabling the reaction between two molecules and a second set of layers having different spacing and/or thicknesses may be configured to adsorb a product of the reaction, thus prolonging the length of the chemical reaction.

In further implementations, an architectural construct can be electrically charged (e.g., as discussed in U.S. patent application Ser. No. 12/857,515) to catalyze a reaction proximate the architectural construct. For example, an architectural construct can be configured to resonate acoustically at a particular frequency, causing molecules to orient themselves in a way that catalyzes a reaction. Moreover, the molecules may be oriented to enable a chemical reaction or their adsorption onto the layers. In some implementations, an architectural construct is configured to transmit or absorb radiant energy to catalyze a reaction. For example, a first set of layers may be configured to absorb radiant energy and transform the radiant energy into heat that a second set of layers having different spacing and/or thickness uses to facilitate an endothermic reaction. In other implementations, a catalyst is added to an architectural construct to catalyze a reaction proximate to the construct. The catalyst may be applied on the edges of layers of the construct or on the surfaces of the construct. For example, chromia may be applied on the edges of an architectural construct, and the chromia may catalyze a chemical reaction between methane and ozone produced from air using ionized ultraviolet radiation or an induced spark.

6. Features Relating to Capillary Properties that Affect the Collector Portion Additional factors that affect whether and how a collector portion configured as an architectural construct will collect or load portions of a target substance include the capillary properties of the collector portion. For example, an architectural construct with parallel layers may be arranged or configured so that liquid moves between its layers via a capillary action. Any of a number of variables can be changed so that the parallel layers can perform a capillary action with respect to a particular substance. In some implementations, the layers' composition, dopants, spacing, and/or thicknesses are selected so that an architectural construct performs a capillary action with respect to a particular target substance. For example, the distance between the individual layers are selected so that the architectural construct performs a capillary action with respect to a particular substance. In a particular embodiment, each concentric layer of the architectural construct may be spaced a capillary distance apart from one another for water and the architectural construct can force water up the construct via capillary action.

An architectural construct may be comprised of some layers that are a first capillary distance or spacing for a first molecule and other layers that are a second capillary distance or spacing for a second molecule. For example, a first set of layers may be a capillary distance with respect to a first molecule, such as propane, and a second set of layers having a different spacing and/or thickness of individual layers may perform a capillary action with respect to a second molecule, such as hydrogen. Additionally, in some implementations, an architectural construct is configured so that heat can be transferred into or out of the construct to facilitate capillary action. In still further embodiments, a charge can be applied to the layers of an architectural construct to facilitate the capillary action.

Figure 5A:
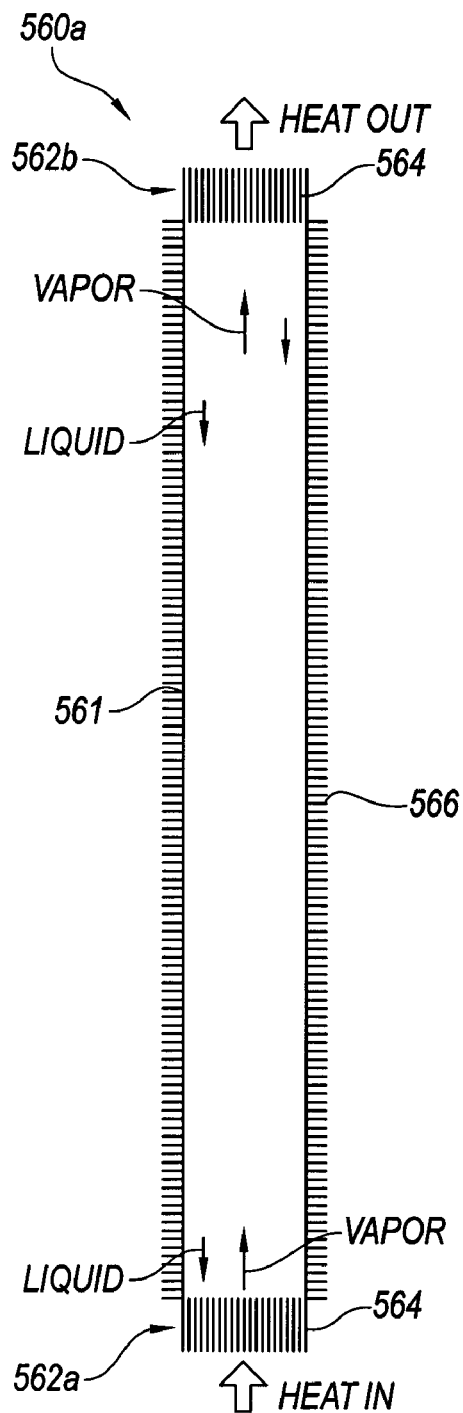
FIGS. 5A and 5B are schematic side views of systems configured in accordance with additional embodiments of the disclosure.

FIG. 5A is a schematic side view of a system 560a configured in accordance with an embodiment of the disclosure. The system 560a includes a heat pipe 561 configuration having a first input end portion 562a opposite a second end output end portion 562b. The first and second end portions 562 can each include a plurality of spaced apart parallel first layers 564 of an architectural construct. In the illustrated embodiment, the first layers 564 at the end portions 562 are oriented in a direction that is aligned with or generally parallel to a longitudinal axis of the heat pipe 561. The heat pipe 561 further includes a plurality of spaced apart parallel second layers 566 extending laterally away from a mid portion of the heat pipe 560a. The second layers 566 extend from the heat pipe 561 at an angle that is generally transverse to the longitudinal axis of the heat pipe 561. The first layers 564 and the second layers 566 are externally accessible to the system and configured to selectively draw predetermined materials or portions of a sample into or out of the heat pipe 560a. These layers can also transfer heat into and out of the heat pipe 561. For example, in operation heat can be introduced into the heat pipe 561 at the first end portion 562a. The heat at the first end portion 562a causes a working fluid to at least partially vaporize. The resulting vapor travels from the first end portion 562a to the second end portion 562b and condenses at the second end portion 562b. The condensed portions of the working fluid return to the first end portion 562a from the second end portion 562b. Heat is transferred out of the second end portion 562b of the heat pipe 560a as result of the condensation of the working fluid at the second end portion 562b.

According to certain features of the illustrated embodiment, as heat leaves the heat pipe 560a, at least a portion of a target sample or predetermined constituent can also be removed via the first layers 564 from the solution at the second end portion 562b (e.g., vapor) as it is brought to the top or second end portion 562b of the heat pipe 560a. Moreover, the second layers 566 can transfer heat in addition to a portion of the target sample or predetermined constituent from the condensate liquid as the condensate travels from the second end portion 562b to the first end portion 562a. In certain embodiments, for example, the working fluid in the heat pipe 561 can be water, and the first layers 564 and/or the second layers 566 can remove methane or other solubles (e.g., carbon dioxide) from the water. In other embodiments, the first layer 564 and/or the second layers 566 can be preloaded with predetermined dopants or materials to adjust the surface tension of adsorption along these surfaces.

Figure 5B:
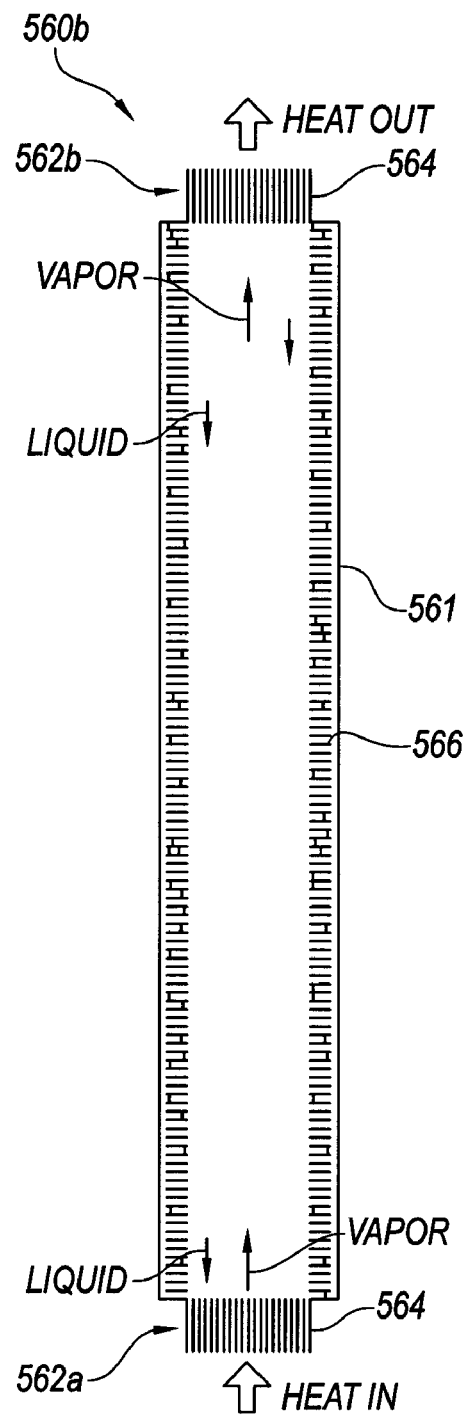

FIG. 5B is a schematic side view of a system 560b configured in accordance with another embodiment of the disclosure. The system 560b includes a heat pipe 561 that is generally similar in structure and function to the heat pipe described above with reference to FIG. 5A. For example, and as shown in FIG. 5B, the heat pipe 561 includes a working fluid enclosed between a first end portion 562a opposite a second end portion 562b. The first and second end portions 562 include first layers of an architectural construct that are oriented in a direction generally parallel to a longitudinal axis of the heat pipe 561. The heat pipe further includes second layer 566 extending radially into the heat pipe 561 in a direction that is generally transverse to the longitudinal axis of the heat pipe. The second layers 566 are accordingly disposed at least partially within the heat pipe and can be configured to load or otherwise remove or collect sample portions from the working fluid.

The capillary sorptive properties of the methods and systems disclosed herein can include any of the features of the systems described in U.S. patent application Ser. No. 13/027,244, entitled "THERMAL TRANSFER DEVICE AND ASSOCIATED SYSTEMS AND METHODS," filed concurrently herewith and incorporated by reference in its entirety.

7. Features Relating to Surface Structures that Affect the Collector Portion In still further embodiments, an architectural construct can include one or more surface structures on its surfaces that facilitate the amount and rate of the loading and unloading of target sample substances into and out of the architectural construct. As described in co-pending U.S. patent application Ser. No. 12/857,515, surface structures can be epitaxially oriented by the lattice structure of a layer to which they are applied. As noted above, in some embodiments, they are formed by dehydrogenating a gas on the surface of the layers. In other embodiments, they are coated on a layer before adjacent layers are configured on the construct. The surface structures can include nano-tubes, nano-scrolls, rods, nano-flowers, and other structures. More specifically, a nano-flower structure can absorb molecules of a substance into an area within the structure and adsorb molecules of the target sample on its surface. In some embodiments, the surface structures enable the architectural construct to load a particular compound of a substance. In some embodiments, the surface structures enable the architectural construct to load and/or unload molecules of a substance more rapidly. In some embodiments, a particular type of surface structure is preferred over another surface structure. For example, in some embodiments, a nano-scroll may be preferred over a nano-tube. The nano-scroll may be able to load and unload molecules of a substance more quickly than a nano-tube can because the nano-scroll can load and unload multiple molecules of a substance at the same time while a nano-tube can only load or unload one molecule at a time. In some embodiments, a first type of surface structure loads a first compound and a second type of surface structure loads a second compound. In some embodiments, surface structures are composed of material that is electrically conductive and/or has a high availability for thermal transfer. In some embodiments, the surface structures are composed of carbon.

In certain embodiments, surface structures can be oriented generally perpendicular to the surfaces of the layers of the architectural construct. In other embodiments, at least some of the surface structures are not oriented perpendicular to the surface that they are applied on. For example, at least some surface structures can oriented at different angles (e.g., other than 90 degree angles) from the corresponding surfaces of an architectural construct. A surface structure may be oriented at a particular angle to increase the surface area of the surface structure, to increase the rate that molecules are collected or loaded by the surface structure, to increase a loading or collecting density of the surface structure, and/or to preferentially collect or load a molecule of a particular compound, or for another reason.

In some implementations, surface structures can be configured on an architectural construct and composed of a different material than the architectural construct. More specifically, the layers of the architectural construct may be composed of graphene and the surface structures may be composed of boron nitride. The surface structures can be composed of other materials, such as boron hydride, diborane ($B_2H_6$), sodium aluminum hydride, $MgH_2$, LiH, titanium hydride, and/or another metal hydride or other suitable compounds.

D. Embodiments and Features of Sensing Portions of a System

As described above with reference to FIG. 1, the sensor portion 104 of the system 100 is configured to detect and/or analyze the presence of one or more portions (e.g. microscopic or molecular portions) of a target sample, as well as detect and/or analyze one or more properties or characteristics of the portions of the target sample. The sensor portion 104 can be integrally formed with the other portions of the system 100, including for example, the collector portion 102. As further described in detail below, the sensor portion 104, and more specifically the detector portion 106 and the analyzer portion 108, can detect and/or analyze properties of a target sample through various mechanisms and or methods.

For example, the method and structure for detecting and analyzing the properties of the target sample can be related to the method and structure that was used to collect or otherwise accumulate the sample. In some implementations where the sample (e.g., microscopic or molecular) portion is loaded between layers of an architectural construct, the detection and/or analysis can include the rate that the sample is loaded between the layers. The detection and/or analysis can further include the depth or length that the sample travels into the architectural construct between the layers. More specifically, the sample, loading rate and/or depth can be indicative of particular target samples, or of particular properties of a target sample. In still further embodiments, the sensing can include examining the remaining products of the target sample after selectively removing specific constituents or other portions from a target sample.

In other embodiments, the optical properties of the collection can provide useful information for the sensing determinations. For example, and referring to the selective surfaces described in detail above, the transmissivity, reflectivity, and/or refraction can be indicative of the presence of the target sample or of the properties of the target sample. In certain embodiments directed to the wavelength shifting, for example, the target sample may emit energy at a first wavelength associated with a first color that is different from a second wavelength associated with a second color of the energy that is transmitted, absorbed, reflected, and/or refracted according to the embodiments described herein. This wavelength change or color change can accordingly provide useful information regarding the target sample, including, for example, the presence of the target sample and/or what the target sample is made from. Similarly, the difference in the angle deflection of incident wavelengths and reflective wavelengths can prove useful. For example, photodetected material such as silicon, gallium, arsenide, etc. can be deposed into pattern in the architectural construct to facilitate the optical sensing of collected radiant energy. Moreover, the temperature of the phase change of the target sample can also be used to detect information regarding the target sample, and in particular with reference to rapid heat input to the target sample. A further useful technique for sensing (e.g., detecting and/or analyzing) a collected target sample includes inductively generating a magnetic or electrical field to see the effect on the target sample. For example, varying the frequency of an electrical field and monitoring the behavior inn light of the varying frequency can additional prove determinative of the presence and/or type of target sample.

In still further embodiments, the sensing portion 104 of the system 100 described above with reference to FIG. 1 can include one or more microprocessors. For example, an architectural construct as disclosed herein can be designed to utilize one or more of the properties discussed above to achieve particular results or outcomes on a microscopic level. Among the applications for which architectural constructs are useful include as a charge processor, a molecular processor, and/or as a bio processor. An architectural construct configured as a charge processor can be used to build microcircuits, detect the presence of a particular atom or molecule in an environment, or achieve another result. In some implementations, an architectural construct configured as a charge processor forms an electrical circuit. For example, parallel layers of graphene can be spaced apart by dielectric materials so that the architectural construct stores an electric charge and functions like a capacitor. In some implementations, an architectural construct can be configured as a high temperature capacitor by isolating parallel layers of the construct with a ceramic. In other implementations, an architectural construct can be configured as a low temperature capacitor by isolating parallel layers with a polymer. In still further implementations, an architectural construct can be configured for processing ions. For example, the architectural construct can be configured with a semi-permeable membrane covering the zones between the layers of the construct. The semi-permeable membrane allows particular ions to penetrate the membrane and enter the architectural construct where they are detected for a particular purpose. In some implementations, an architectural construct is configured as a solid-state transformer.

Additionally, in some implementations an architectural construct can transform electromagnetic waves at a molecular scale. For example, an architectural construct can be configured to transform 100 BTU of white light into 75 BTU of red and blue light. The white light is wave-shifted by chemically resonating the white light to transform it into the blue and red light. Moreover, the architectural construct can be composed of carbon with selected zones converted to a solid solution or compound such as a carbide with reactants such as boron, titanium, iron, chromium, molybdenum, tungsten, and/or silicon, and the architectural construct can be configured so that the layers are oriented to shift white light into desired wavelengths such as red and/or blue light and/or infrared frequencies.

An architectural construct configured as a bio processor may be used to create enzymes, carbohydrates, lipids, or other substances. In some implementations, an architectural construct is configured as parallel layers and it removes a product of a biochemical reaction from a reaction zone so that the biochemical reaction can continue. For example, an architectural construct may be configured to load a toxic substance, like alcohol, from a reaction zone within a corresponding support tube that supports the layers. By removing the toxic substance, a microbe involved in the biochemical reaction will not be killed and the biochemical reaction can continue unabated. In other implementations, an architectural construct can be configured to remove a useful product of a biochemical reaction from a reaction site without having to interrupt the reaction. For example, the support tube within the architectural construct may house a biochemical reaction that produces a useful lipid, which is loaded into the zones between the layers of the construct and unloaded on the outside edges of the zones. Therefore, according to these embodiments the biochemical reaction can continue while the useful product is removed.

E. Embodiments and Features of Communication and Controller Portions of a System As described above with reference to FIG. 1, the communication and controller portion 109 including the reporter portion 110 and/or the controller portion 111 of the system 100 is configured to provide a real-time or automatic signal or other suitable indication relating to the collection, detection, and/or analysis of the target sample. The reporter portion 110 can be at least partially composed of an architectural construct as described in detail above. In certain embodiments, the reporting can include sending or transmitting a signal (e.g., via a wired or wireless medium) to a controller or another similar system indicating the presence of the detected target sample or the results of the analysis of the one or more properties of the target sample. In other embodiments, the signal can include an indication of an appropriate action in response to the sensed target sample. For example, the signal can include information regarding preventative maintenance or safety relating to the target sample, as well as information relating to the location, quantity, concentration, or other property of the target sample. Moreover, the reporting signal can be sent simultaneously or otherwise in real-time with the sensing of the target sample, or the reporting signal can be stored and transmitted at a later time. Several embodiments of suitable components and configurations for reporting the indication of the detection or analysis of the target sample are described in detail below. Furthermore, the results reporting can be tailored to the specific target sample that is being acquired. For example, the reporting signal can include diagnostic or preventative information relating to the target sample. Communicating the analysis results of the target sample can provide several advantages. For example, the communication can be in real-time and based off of microscopic portions of the target sample. This greatly differs with conventional detection techniques that may require obtaining a relatively large portion of a sample, shipping the sample to a laboratory, and waiting for analysis results, all the while risking contamination of the sample.

According to certain implementations, an architectural construct can include a microprocessor as described in detail above. In these instances, an electrical current from one or more optical sensors can communicate with the microprocessor to emit a signal or provide another suitable indication of the results. Moreover, the architectural construct can include one or more nano-radios for emitting the results signal. The system can accordingly provide the result signal either locally or remotely from the target sample source.

F. Embodiments and Features of Clearer Portions of a System

As described above with reference to FIG. 1, the clearer portion 112 of the system 100 is configured to clear, unload, or otherwise remove the collected portions (e.g. microscopic or molecular portions) of the target sample. The clearer portion 112 can be at least partially composed of an architectural construct as described in detail above. Moreover, the clearer portion 112 can be integral with any of the other portions of the systems described herein including, for example, the collector portion 102, the sensor portion 104, and/or the reporter portion 110. In some implementations, the mechanism or method that the clearer portion 112 utilizes to remove the collected target sample can be related or dependent upon the mechanism or method that was used to collect or load the target sample. Suitable methods for clearing the target sample can include, for example, applying a pressure gradient to the portion of the architectural construct holding the target sample. Such a pressure gradient can include, for example, a release of pressure or a building up of pressure, resulting for example, from electrolysis, a mechanical pump, etc. In still further embodiments, micro-electrolysis can be implemented with aqueous and non-aqueous media to clear or otherwise withdraw the target sample. For example, the electrolyzing media can be selected depending on the composition of the target sample.

According to additional embodiments of the disclosure, a predetermined gas or fluid can be used by the clearer portion 112 of FIG. 1 to clear or flush the accumulated target sample from the collector portion 102. In one embodiment, for example, hydrogen can be used to clear collection zones between spaced apart layers of an architectural construct. Moreover, when hydrogen flushes or clears the collection zones, at least a portion of the hydrogen can remain in these zones. The remaining or loaded hydrogen can have a first affinity to be retained between these layers, however the remaining hydrogen can be replaced by another collected target sample that has a second affinity, which is greater than the first affinity, to load in the collection zones between the layers of the architectural construct. In yet other embodiments, the clearing of the accumulate target sample from the collector portion 102 can be accomplished or aided by plasma, capacitive, hydrogen, oxygen, and/or steam flushing of the of the collector portion 102.

Figure 6A:
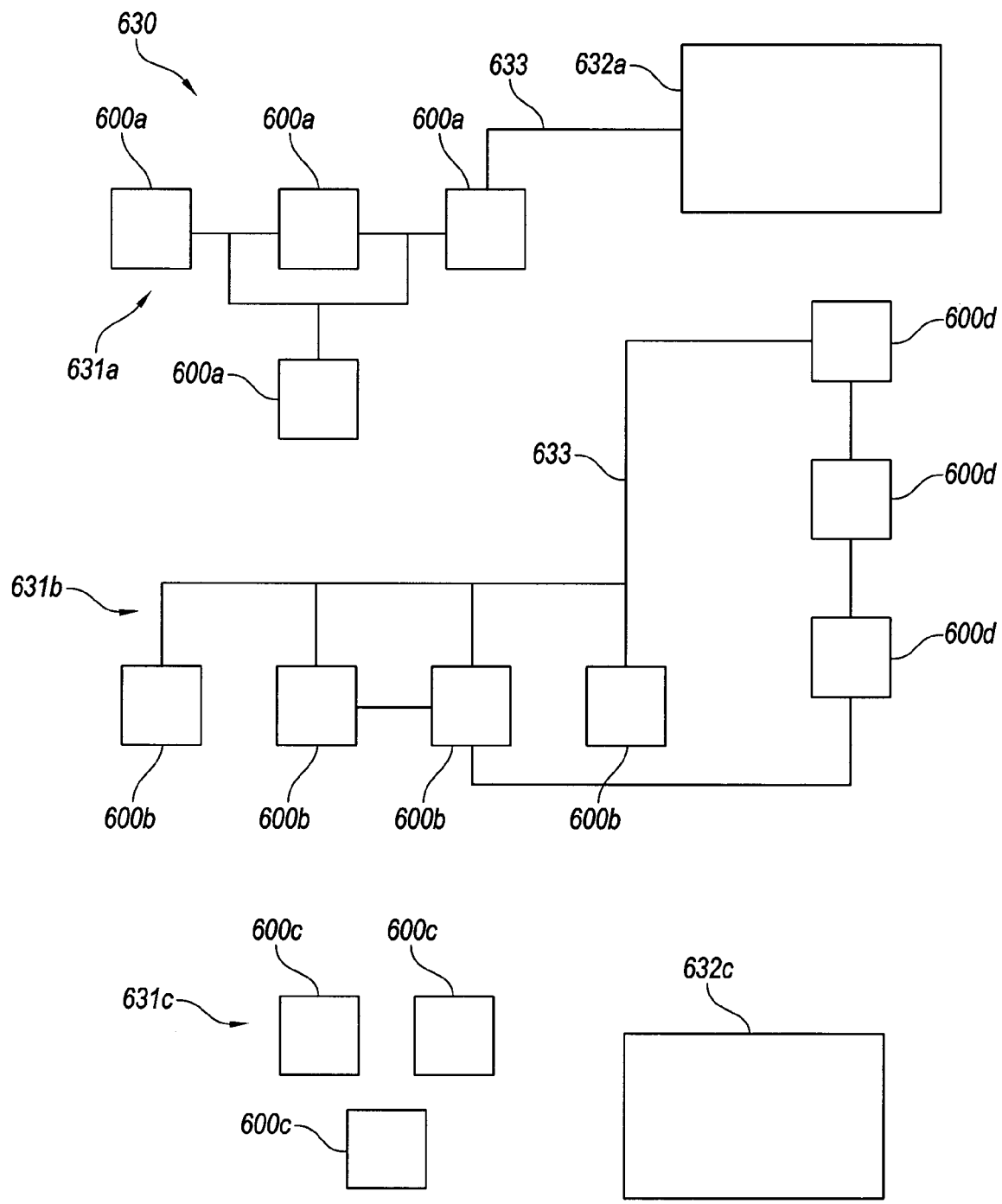
FIG. 6A is a schematic diagram of a network or system configured in accordance with embodiments of the disclosure.

G. Additional Embodiments of Systems, Components, and Methods for Collecting, Sensing, Reporting, and/or Clearing Portions of a Target Sample According to additional embodiments of the present disclosure, the systems and methods disclosed herein can be used in a variety of environments. For example, systems for collecting a microscopic portion of a target sample, sensing (e.g., detecting the presence of the sample and/or analyzing properties of the sample), reporting an indication of the sensing, and/or clearing the target sample, can be performed in a variety of environments and for a variety of purposes. The embodiments described herein can use one or more sensors including, for example, sensors with collector, sensor (e.g., detection and analysis), reporter/controller, and/or clearer portions as described above with reference to FIG. 1. For example, the systems, sensors, and associated reporting described herein can be part of an interconnected system or network. FIG. 6A, for example, is a schematic diagram of a network or system 630 configured in accordance with embodiments of the disclosure. In the illustrated embodiment, the system 630 includes multiple groups of collector/sensor/reporter/clearers ("sensors") including the features as described herein, including, for example, the system 100 described above with reference to FIGS. 1-2B. Referring to FIG. 6A, for example, the system 630 includes a first node or group 631a of first sensors 600a, a second node or group 631b of second sensors 600b, and a third node or group 631c of third sensors 600c. Some of these sensors 600 can be connected to each other or otherwise configured to communicate with each other via a wired connection 633. Other sensors, however, such as schematically illustrated with the third sensors 600c, any of the sensors can communicate wirelessly. According to additional features of the illustrated embodiment, the first group 631a includes a first controller 632a that is coupled (e.g., wired, wirelessly, etc.) to one or more of the first sensors 600a. Moreover, the third group 632c includes a third controller 632c that is wirelessly coupled to one or more of the third sensors 600c. Moreover, any of these controllers and sensors can be coupled (e.g., wired, wirelessly, etc,) to other sensors and/or controllers in other groups. In addition, several of the sensors 600 can be positioned on or near the same structural component for the purpose of collecting and analyzing the same target sample. In other embodiments, however, different sensors 600 can be positioned at different locations or on different structures for the purpose of collecting and analyzing data relating to different target samples. In still further embodiments, one of the controllers 632 can operate as a controller for all of the groups 631 or all of the sensors 600 in the entire system. Moreover, one or more of the controllers 632 can operate as a relay to communicate information and/or receive instructions or information from a remote controller. According to additional embodiments of the present disclosure, the system 600 is scalable to collect, analyze, and communicate data in any sized environment, including, for example, international or global environments.

The system 630 illustrated in FIG. 6A accordingly illustrates a network or system of interconnected sensors 600 and controllers 632 that can be configured to communicate with one another and/or to provide feedback for various environments. For example, the sensors 600 illustrated in FIG. 6A can be used in various systems, applications, and/or environments such as in a school, hospital, public transportation (airplane, bus, train, metro, etc.). They system 630 could additionally be used in applications such as quality assurance, preventative maintenance, safety (including trend analysis), hazard warnings (including shut down procedures), chemical identification and surveillance, environmental monitoring, homeland security, hazardous material transportation and monitoring, pollution detection systems, etc.

Further, the system 630 illustrated in FIG. 6A accordingly illustrates a wide-area network of interconnected sensors 600 and controllers 632 that can be configured to enable scalability of regional, national, international and global networks for data acquisition of microscopic chemical sampling, information processing, trend analysis, and/or prediction related to earth science, environmental protection, public health and economics. Any of the sensors 600 can be geo-sensors, which can be defined as any device receiving and measuring environmental stimuli that can be geographically referenced. Such geo-sensors include inertial or accelerometer sensors to provide a record of the movements of a device or system including, for example, seismic and longer motions. More specifically, one or more sensors or geo-sensors as disclosed herein can be carried by a device that travels to various locations. The sensors and/or geo-sensors accordingly enable interrogation and verification of the device's travels with respect to the time of each travel and location of each event, thereby providing a distinct identity or signature of the locations and/or travels of the device using, for example, seismic data. Although, large-scale networks of sensors have been attempted for several decades in such examples as the World Meteorological Organization for measuring weather and climate patterns, and the Argos network of buoys for measuring temperature and salinity of the world's oceans, these networks have not achieved real-time chemical surveillance and have been limited in the chemical information that they can identify and report. According to embodiments of the present disclosure, however, the one or more networked systems of sensors 600 and controllers 632 are applicable for use with weather ships and planes deployed sensors, ocean data buoy sensors, surface-land weather station sensors, upper-atmosphere stations and weather-balloon deployed sensors, etc.

One advantage of the present disclosure for environmental and/or geospatial monitoring is to enable acquisition of chemical information which can be geographically referenced and then reported in a continuous real-time stream, or a programmed time-sequenced batch report, or event triggered reporting (such as a hazard warning) of chemical information over widely dispersed areas. This wide-array of sensor data can be configured to communicate and exchange information through interoperability arrangements such as the Internet, and thereby (a) obtain geographically referenced chemical information which previously was unavailable or too costly to obtain with regularity, and (b) obtain the needed volume and distribution of data sources that enable conversion of data into information usable for public policy decision-making. For instance, the Global Earth Observation System of Systems (GEOSS) is overseen by the Group on Earth Observations (GEO), an intergovernmental organization comprised of seventy-three nations, the European Commission and fifty-two international organizations, whose goal is to promote scientific connections between observation systems that constitute the system of system. The use of sensor networks as disclosed herein revolutionizes the way in which geospatial data is acquired. In another example of particularly useful application of the embodiments described herein, in 2000, the United Nations Environment Programme (UNEP) advanced the "Digital Earth" project (first presented by US Vice President Al Gore in 1998, describing the virtual representation of the Earth that is spatially referenced and interconnected with the world's digital knowledge archives), to enhance decision-makers' access to global environmental information in association with economic and social policy issues. In a further example, the economic problem of Greenhouse Gas Emissions control has led to various programs for carbon-credit economic incentives to motivate corporations to use industrial processes which will reduce or eliminate harmful emissions. More specifically, a wide-spread criticism of this international effort is the lack of adequate safeguards against fraud or widespread "gaming-the-system" without measurement of actual time of each travel, correlation to seismic events and other environmental data empirically linked to specific industrial behavior and specific government policy. Embodiments of the present disclosure, however, solve this problem by allowing microscopic chemical sampling to be widely disbursed so as to enhance at least the following measurement benefits of tracking and assessment: Energy (bio-energy, bio-mass, wind, hydro power, geothermal, solar, etc.); Climate (land, ocean and atmosphere changes, Greenhouse Gas Emissions, water and energy exchanges, etc.); Water (resources, quality, and land-water use patterns); Weather (atmosphere changes of wind, temperature, cloudiness, moisture, pressure, etc. affecting land, ocean, and vegetation, etc.); Ecosystems (health and stressors affecting macro and micro systems, interrelated needs of living systems); Agriculture (cultivation patterns, forestry, and land degradations, etc.); Biodiversity (ecosystem characteristics indicative of their survivability, including habitat fragmentation, animal and vegetative species extinction rate and factors, etc.); Disaster Response and Mitigation (fire monitoring, land-ocean-atmosphere degradation, early warnings of fire, flood, earthquakes, landslides, mudslides, hurricanes, tornadoes, etc.); and/or Public Health (land, vegetative and animal changes, disease vectors, boundary conditions, etc.).

Figure 6B:
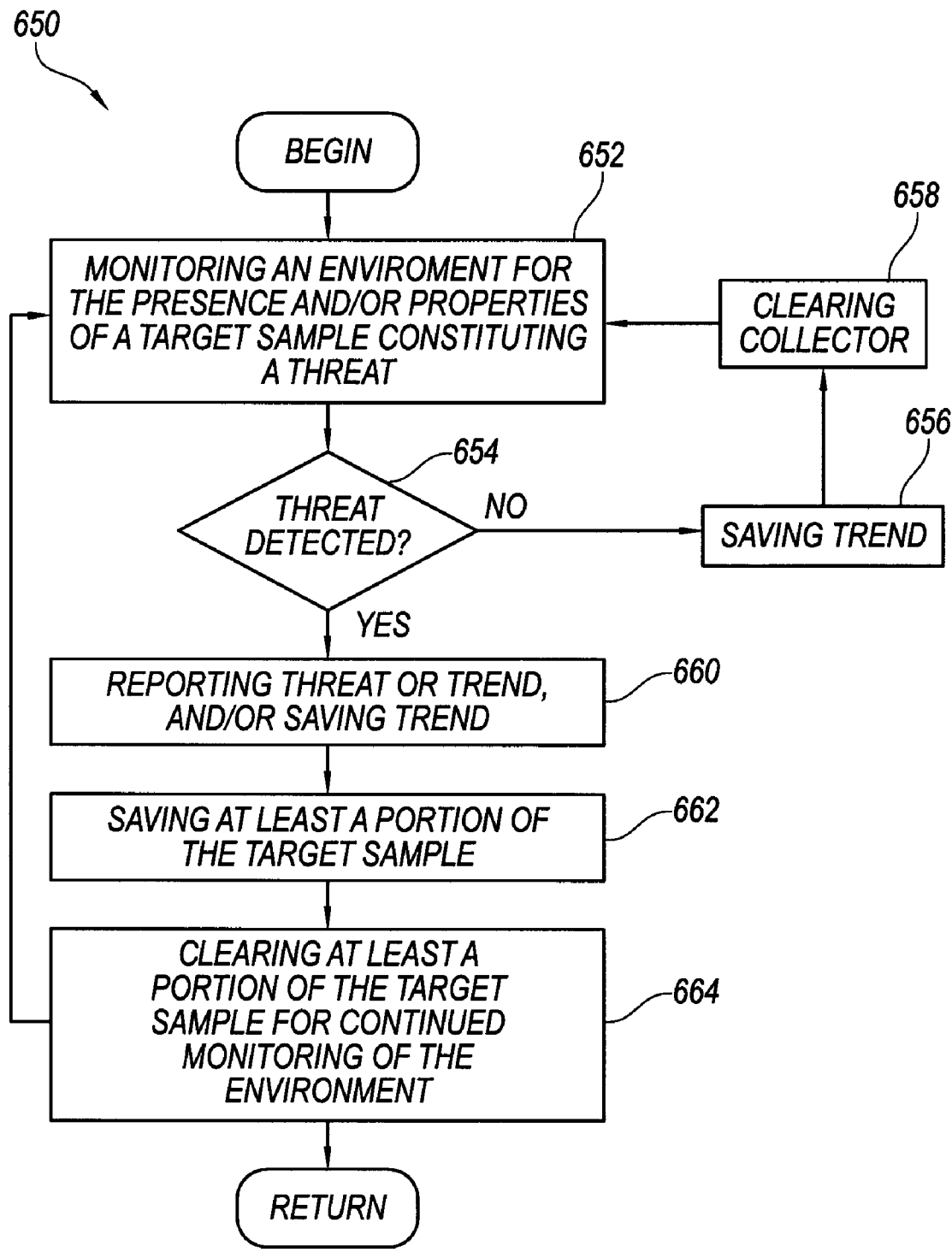
FIGS. 6B and 6C are flow diagrams of methods configured in accordance with additional embodiments of the disclosure.

FIG. 6B is a flow diagram of a process or method 650 for use in a homeland security application or environment to detect a potential threat, or in other locations or environments suitable for a wide area network surveillance, including for example chemical surveillance. For example, the method 650 includes monitoring an environment for the presence of and/or properties of a target sample constituting a threat (block 652). The monitored environment can include a public environment such as an airport, train station, bus station, other public transportation, shopping mall, sports stadium or sports venue, government buildings, etc. Moreover, a network of multiple sensors as described herein with reference to the network array shown in FIG. 6A can be arranged throughout the environment to monitor the target sample. Moreover, individual sensors can include a controller and/or the network can include a central controller that can communicate with the individual sensors. The sensors can be placed in a network throughout the environment to effectively monitor for the target sample. For example, with reference to an airport environment, one or more sensors can be positioned at baggage claim, screening or security checkpoints, walkways, boarding gates, on the planes, etc.

A threat can constitute any unwanted or undesired target sample within the environment, including, for example, toxic or dangerous target samples. At decision block 654, the method includes determining if a threat is detected, e.g., by the presence of the target sample, one or more properties of the target sample, accumulation rates or quantities of the target sample, etc. In certain embodiments, the individual sensors can locally or independently determine if the target sample constitutes a threat. In other embodiments, however, the individual sensors can send data relating to the collected and/or analyzed target sample to the central controller so that the central controller can determine if the target sample constitutes a threat. If no threat is detected (e.g., by the central controller or one or more of the individual networked sensors), the method 650 includes saving a trend related to the collection and/or analysis of the target sample (block 656). The trend can include the accumulated quantity of the target sample, accumulation rate, accumulation location, type of target sample, etc. Moreover, the trend can be saved locally on the individual sensor that collected the portion, as well as at a central controller that receives an indication of this information from the sensor. After saving the trend, the method can further include clearing at least a portion target sample from the sensor (block 658), and continuing to monitor the environment (return to block 652). In certain embodiments, to clear the collected portion from the sensor, the central controller can send a signal to the sensor to instruct the sensor to clear the sample.

If a threat is detected, the method 650 includes reporting the threat or trend from the sensor to the central controller, and/or saving the trend either at the local sensor or at the central controller (block 660). The method 650 can also include saving a least a portion of the collected portion of the target sample at the sensor 662. In addition, the method 650 can further include clearing at least a portion of the target sample for continued or cyclic monitoring of the environment (block 664). Although the method 650 described above is applicable to a homeland security environment, those of ordinary skill in the art will appreciate that the method 650 can be used for other applications or in other environments, including, for example, monitoring substances that do not constitute a threat.

Figure 6C:
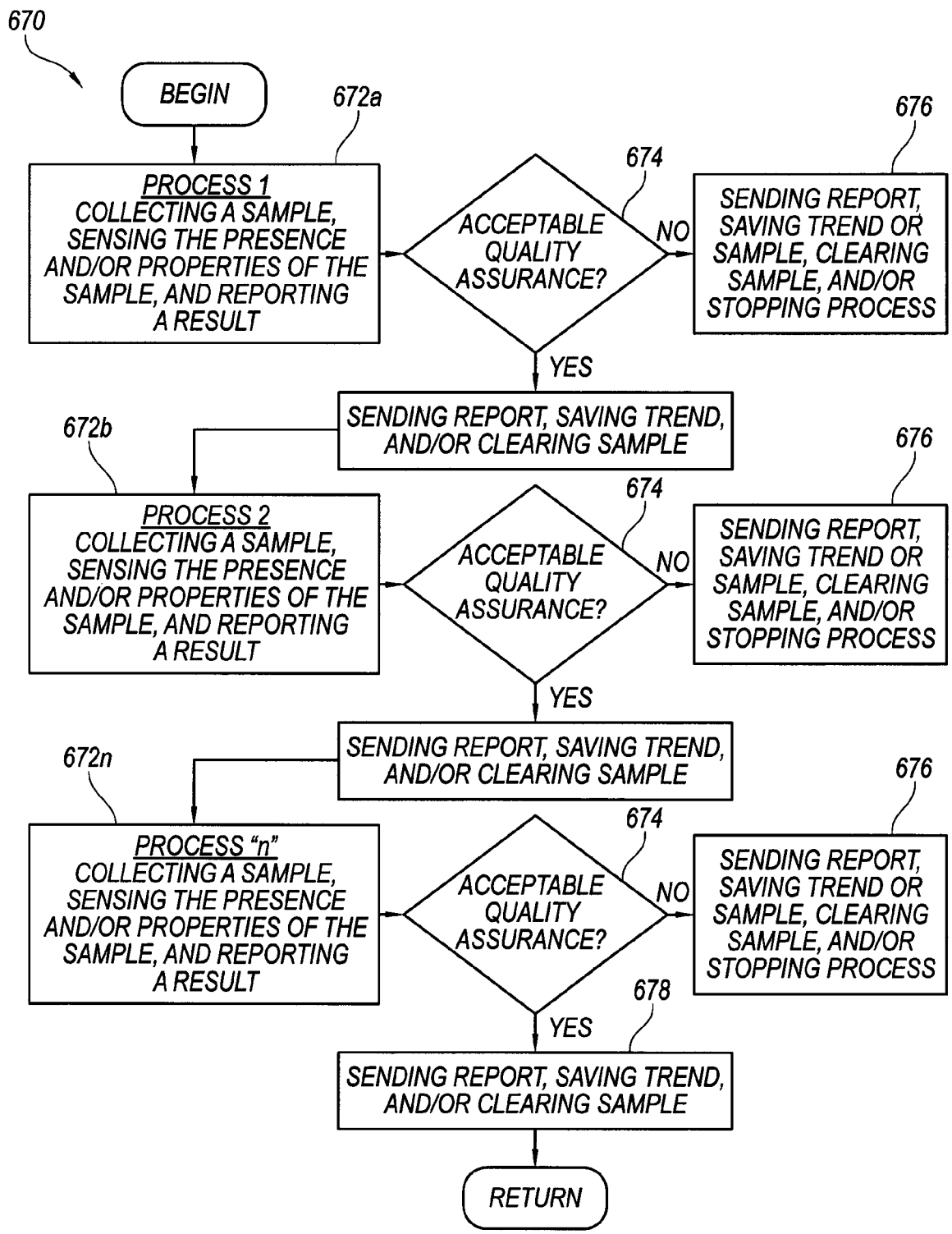

FIG. 6C is a flow diagram of another process or method 670 for use in a quality assurance application or environment to detect acceptable levels of quality or a target portion or product (e.g., purity or presence of a chemical or ingredients, etc.). For example, the method 670 can be used for multiple processes or sub-routines in which a collection, sensing, reporting, and/or clearing event occurs before the next process or sub-routine begins. More specifically, the method 670 includes, in a first process or sub-routine in a process (e.g., "process 1"), collecting a sample, sensing the presence and/or properties of the sample, and reporting a result of the sensing (block 672a). The method 670 also includes determining if the first process results in an acceptable level of quality assurance (decision block 674). If the quality assurance is not acceptable, the method 670 includes sending a report of the unacceptable quality, saving a trend of the collected sample (e.g., accumulation rate, quantity, type, etc.), clearing at least a portion of the sample, and/or stopping the first process (block 676).

If the quality assurance is acceptable, the method 670 includes allowing a second process or sub-routine in a second process to proceed (e.g., "process 2") and collecting a sample, sensing the presence and/or properties of the sample, and reporting a result of the sensing (block 672b). With reference to the second process, the method 670 includes the same steps as indicated above at blocks 674, 676, and/or 678. If the quality assurance is acceptable in the second process, the method 670 includes allowing another process or sub-routine in another process to proceed (e.g., "process n") and collecting a sample, sensing the presence and/or properties of the sample, and reporting a result of the sensing (block 672n). The $n^{th}$ process is intended to indicate as many processes as a designer wishes to include in the method 670. With reference to the $n^{th}$ process, the method 670 includes the same steps as indicated above at blocks 674, 676, and/or 678. The method 670 can include cycling back to the first process or continuing with a predetermined number of other processes.

In other embodiments, systems for collecting a microscopic portion of a target sample, sensing (e.g., detecting the presence of the sample and/or analyzing properties of the sample), reporting an indication of the sensing, and/or clearing the target sample, can be used for a variety of other applications including, for example, safety including trend analysis, hazard warning including shut down procedures, preventative maintenance, clean room monitoring and clean room standards maintenance, communication with existing or external computer networks including RFID systems, homeland security including threat detection, prediction and identification of the source of attack, drug trafficking, human trafficking, terrorist monitoring, firearm, alcohol, and drug enforcements, as well as shipping industries including container movement, food chain transport, manufacturing processes, chemical industry processes, medical delivery process, pharmaceutical manufacturing process, fuel management and safety, natural gas pipeline safety and quality, carbon credit recording and reporting, and/or olfactory medical diagnosis. With reference to carbon credits, for example, the methods and systems disclosed herein can provide reliable and convenient methods of tracking and reporting carbon credits. In other embodiments, the systems and sensors disclosed herein can include inertial sensors to track location and/or geographic data relating to the sensor.

In still further embodiments, the systems and sensors disclosed herein can be used in at least the following environments: shipping industries (including, e.g., container movement by truck, rail, and/or marine); natural gas pipeline quality and safety; the Office of Homeland Security (including, e.g., terrorist monitoring, threat detection, prediction and identification of the source of attack, safety of public transportation system such as airports, buses, boats, ships, trucks, rail, interdiction of human trafficking etc.); firearm, alcohol, and drug enforcements (including, e.g., interdiction of drug trafficking); fluid supply or distribution systems (including, e.g., water supply and distribution); food production, packaging, and transport systems; manufacturing processes (including, e.g., chemical industry manufacturing processes, pharmaceutical manufacturing processes, etc.); medical delivery processes (including, e.g., assurance of correct medication delivery, olfactory medical diagnosis, etc.); fuel management and safety; carbon credit recording and reporting of greenhouse gas emissions; Environmental Protection Agency toxic emission monitoring; and/or clean room monitoring and clean room standards maintenance.

In still further embodiments, these systems and sensors can be used for specific medical applications. More specifically, in one embodiment, for example, a sensor as disclosed herein can provide an indication as to a T-cell response of a human body to provide an indication of the immune system or immune activity of that body. For example, a medical professional can biopsy an undiagnosed tumor from a patient and provide a portion of the tumor as input to a sensor configured in accordance with embodiments as disclosed herein. The sensor can accordingly determine from a microscopic or molecular sample, if there is a T-cell response from the patient associated with the tumor. Accordingly, the sensor can provide rapid and early information relating to the immune system activity of the patient and/or the tumor. Moreover, a patient's T-cell response is only one example of a suitable determination that is capable according to systems and methods of the present disclosure. For example, in other embodiments these systems can be configured to detect other medical situations or reactions of the body (e.g., developing specific proteins as a result of a specific medical condition, etc.).

Figure 7A:
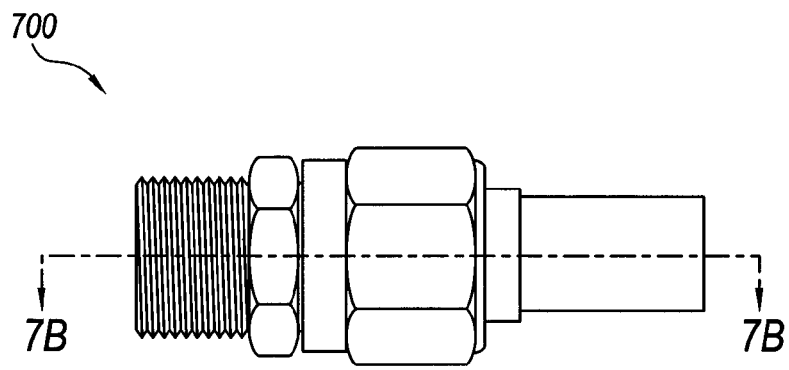
FIG. 7A is a side view of a fitting assembly configured in accordance with an embodiment of the disclosure.
Figure 7B:
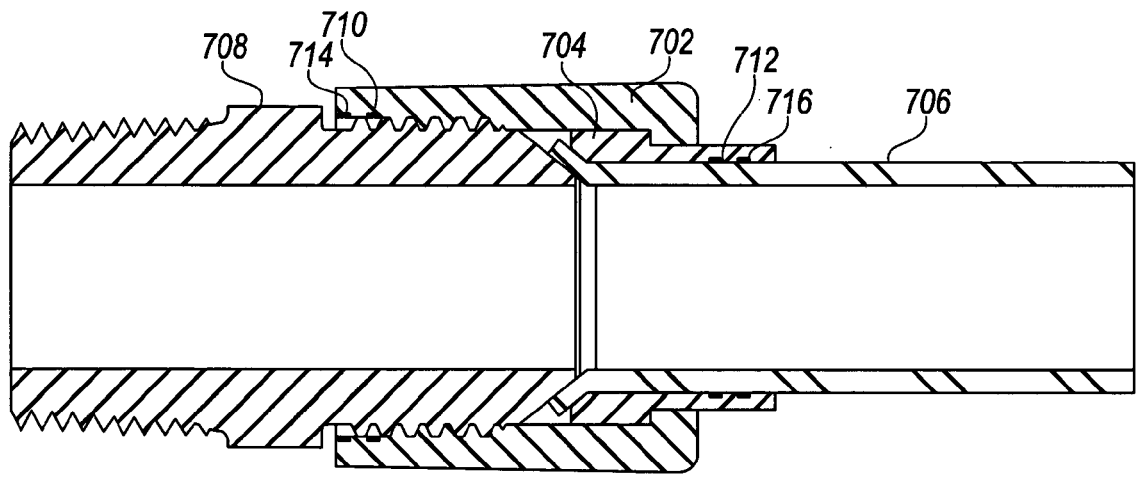
FIG. 7B is a cross-sectional side view taken substantially along lines 7B-7B of FIG. 7A.
Figure 7C:
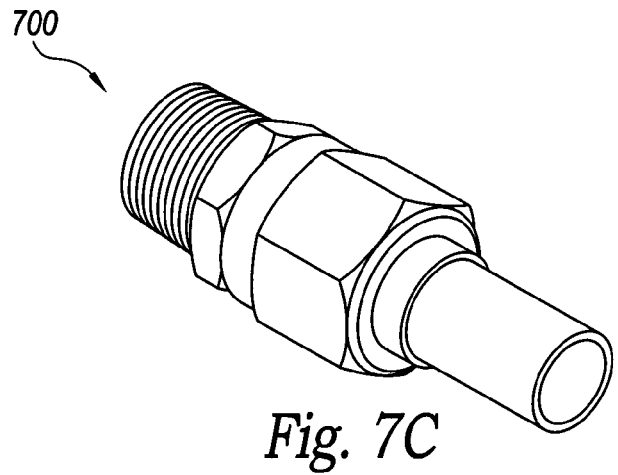
FIG. 7C is an isometric view of the fitting assembly of FIG. 7A.

According to additional features of the present disclosure, the methods and systems disclosed herein include an indicator or sensor that is used in a fitting assembly, such as a fitting assembly attaches to one or more conduits. FIG. 7A, for example, is a side view of a fitting assembly 700 including an indicator configured in accordance with an embodiment of the disclosure. Although several features of the disclosure are described below with reference to the fitting assembly 700, these features can be used with any type of fluid conveying system, including, for example, flexible conduits, rigid conduits, hoses, plugs, nozzles, sprayers, filters, catheters, intravenous conduits, syringes, needles, tire tubes, inner tubes, and/or any other type of component associated with fluid conveying systems or devices. Returning to the Figures, FIG. 7B is a cross-sectional side view of the assembly 700 taken substantially along the line 7B-7B of FIG. 7A, and FIG. 7C is an isometric view of the fitting assembly 700. Referring to FIGS. 7A-7C together, in the illustrated embodiment, the assembly 700 includes a male connector 708 that mates with or attached to a female connector 702 to provide an attachment to a conduit 706. The assembly 700 further includes a "tattletale" element, such as a sensor or an indicator for providing an alarm or other type of indication relating to a fluid flowing through the assembly 700. In the illustrated embodiment, for example, the indicator is carried by the assembly 700 in the vicinity of the connection formed by the male connector 708 and the female connector 702. More specifically, one or more indicators can be carried by the assembly at the locations indicated at 710, 712, 714, and/or 716, as shown in FIG. 7A on the male connector 708 and the female connector 702. Moreover, the male connector 708 and the female connector 702 can include features configured for attachment to or compatible for use with tapered pipe threads, flared, or compression fittings, or other types of conduits. For example, the first part or male connector 708 may include one or more threaded end portions that are axially aligned about a central longitudinal axis of the assembly 700. The second part or female connector 702 may have a female threaded section 710 that can also be axially aligned about the central longitudinal axis. Moreover, in the illustrated embodiment the assembly 700 is attached to the conduit 706 having a flared end portion mated against a corresponding surface of the male connector 708. The assembly 700 also includes a compression seal 704 positioned between the female connector 702 and the conduit 706. When assembled, the female connector 702 urges the compression seal 704 and the flared portion of the conduit 706 tightly against the male connector 708.

In certain embodiments, the tattletale element or indicator can include any type of detector or sensor to detect if and/or when a seal between the fitting assembly 700 and the conduit 706 has failed and leakage of a fluid is beginning to occur. The indicator can provide a visible indication of the leakage, for example, to allow a user to visually inspect the assembly 700 for a leak. For example, the indicator can provide a colored indication of a leak. More specifically, the indicator can release a colored dye upon activation by leaked fluid (e.g., contact with a leaked fluid) or contact with an activation agent that has been added to the fluid flowing through the assembly 700. In certain embodiments, for example, a halogen such as iodine, chlorine, and/or fluorine in water could be the activating agent that reacts with the indicator and causes the release of a liquid (or other indication) from tattletale element indicator 704. In such embodiments, after collecting or contacting relatively few molecules of leaked fluid, the indicator can provide a magnified signal. The signal can include, for example, a readily detectable color, fluorescence, phosphorescence, etc. Moreover, other alarms or tattletale triggering events can include other signals such as radio signals emitted by the indicator resulting from a change in capacitance, resistance, and/or a magnetic field in the indicator induced by the fluid contacting or leaking by the indicator 704.

In another example, the indicator can provide an indication of incipient leakage in response to a transmission of an interrogation signal directed at the indicator 704. In these embodiments, the tattletale component indicator senses chemical, physical, optical, radio, sound, or thermal information to detect incipient leakage and transmit an indication of the leakage. Moreover, the detector can transmit a request for preventative maintenance signals or otherwise interact to an interrogation signal with a reply request for preventative maintenance. Such transmission of data to or from the indicator can include information such as the fitting location, identification, type of fluid, rate or amount of leakage, history of application, etc.

Figure 8A:
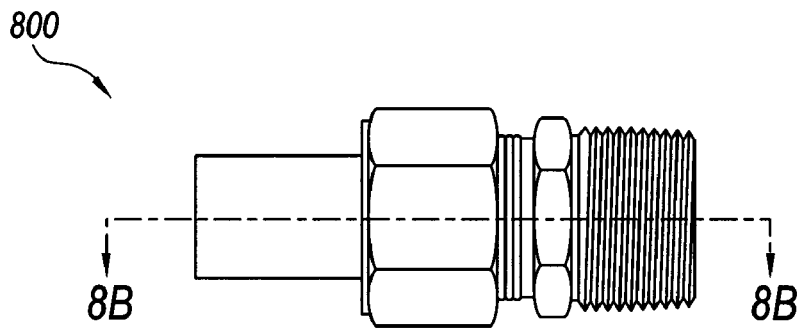
FIG. 8A is a side view of a fitting assembly configured in accordance with another embodiment of the disclosure.
Figure 8B:
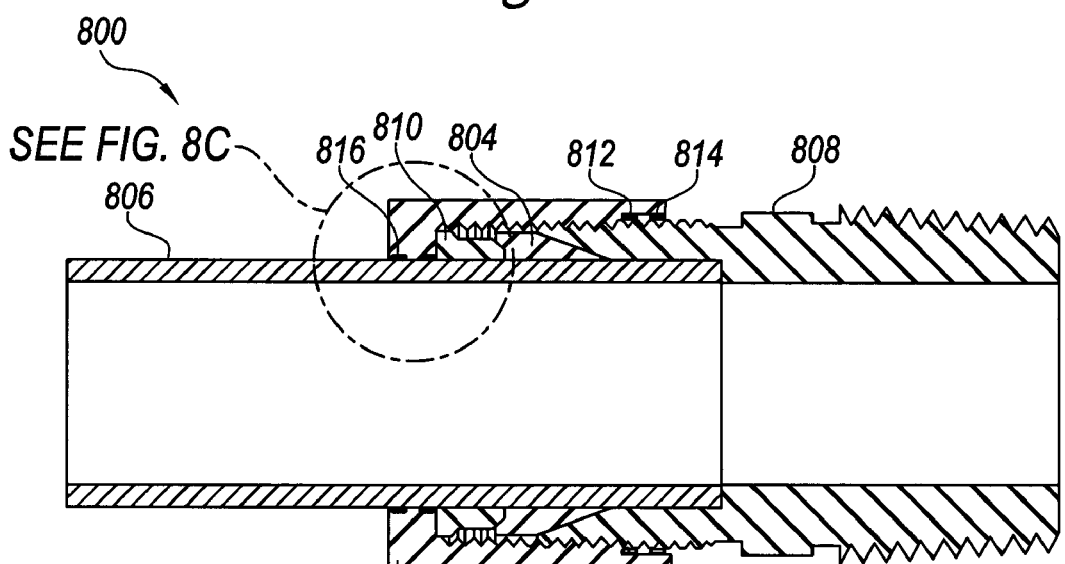
FIG. 8B is a cross-sectional side view taken substantially along the line 8B-8B of FIG. 8A.
Figure 8C:
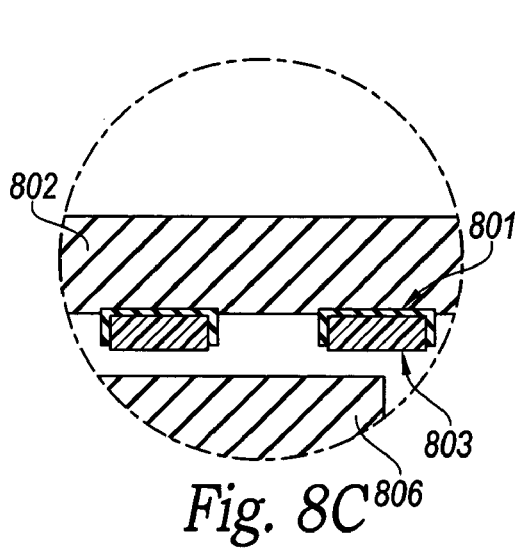
FIG. 8C is an enlarged detail view of a portion of FIG. 8B.
Figure 8D:
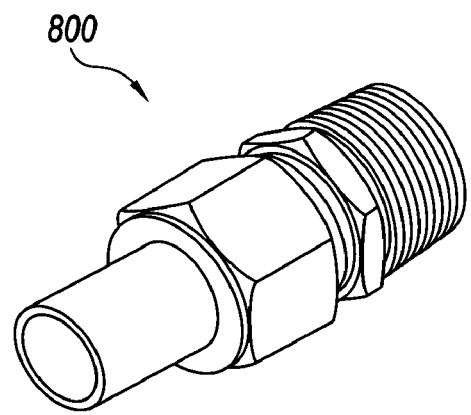
FIG. 8D is an isometric view of the fitting assembly of FIG. 8A.

In certain applications, the indicator includes sensing miniature, micro or nano circuitry, for example at locations 712 and/or 710. The circuitry can be activated by a photovoltaic material that is carried by the assembly 700 proximate to the indicator, for example at locations 714 and/or 716. Consequently if incipient leakage is detected by the detector with a sensor circuit at locations 710 and/or 712, ambient light or an interrogation light source can provide photovoltaic power to the photovoltaic material at locations 714 and/or 716 to activate the circuit at 710 and/or 712. In this manner, the indicator can provide a radio signal or serve in a circuit as a ring oscillator to develop an incipient leak signal that is broadcast or interrogated by non-contact means, including, for example, radio waves or infrared. The following references related to microelectronics, which are incorporated herein in their entireties by reference: http://news.bbc.co.uk/go/pr/fr/-/2/hi/science/nature/4839088: http://www.bio-medicine.org/biology-technology-1/Toward-worlds-smallest-radio-3A-nano-sized-detector-turns-radio-waves-into-music-1330-1/: University of California at Berkeley Physics Department—Nanotube Radio: Supplemental Materials: ScienceDaily-.com—"First Fully-functional RadioFrom A Single Carbon Nanotube Created": PhysicsOrg.com—"Make Way for the Real Nanopod: Researchers Create First Fully Functional Nanotube Radio" and http://www.nanowerk.com/spotlight/spotid=3080.php FIG. 8A is a side view of another assembly 800 configured in accordance with an embodiment of the disclosure. FIG. 8B is a side cross-sectional view taken substantially along the line 8B-8B of FIG. 8A, FIG. 8C is an enlarged detail view of detail 8C of FIG. 8B, and FIG. 8D is an isometric view of the assembly 800. Referring to FIGS. 8A-8D together, the illustrated assembly 800 is configured for compression sealing a tube 806 to a fitting 808. For example, compression of an annular seal 804 is established by tightening of a nut 802 to force axial motion of seal element 804 into the conical receiver at an end of the fitting 808 and to be at least partially swaged to form at least a line of contact seal against tube 806 and a corresponding line of contact seal against the fitting 808. The assembly 800 also includes a tattletale sensor or indicator 810 that can be positioned near or on the seal element 804. The indicator 810 serves as an early tattletale indicator of incipient leakage to delineate and/or broadcast an appropriate maintenance request signal or otherwise provide an indication of a leak in the assembly 800.

In certain embodiments, the assembly 800 can also include one or more detectors at locations indicated at 812, 814, and/or 816, as shown in FIG. 8B. In conjunction with detector 812 and/or 814, component 816 may be responsive to visible, UV, and/or microwave radiation when interrogated to relay and/or otherwise participate in a preventative maintenance signal or request. This enables quick inspection with an illuminating and/or activating light source that detects any distinguished signal from the one or more detectors.

As shown in FIG. 8C, the assembly 800 can also include a detector with one or more leak collectors 803 proximate to one or more miniature circuits 801. The circuits 801 can provide a signal by means selected from the technologies disclosed herein. Miniature, micro, or nano-circuits may similarly be located on or within other suitable locations in the assembly 800, including, for example on a nut 802 as needed to provide redundant assurance of leak detection and signal delineation at the earliest incidence or indication of a leak.

Figures 9A, 9B, 9C, 9D:
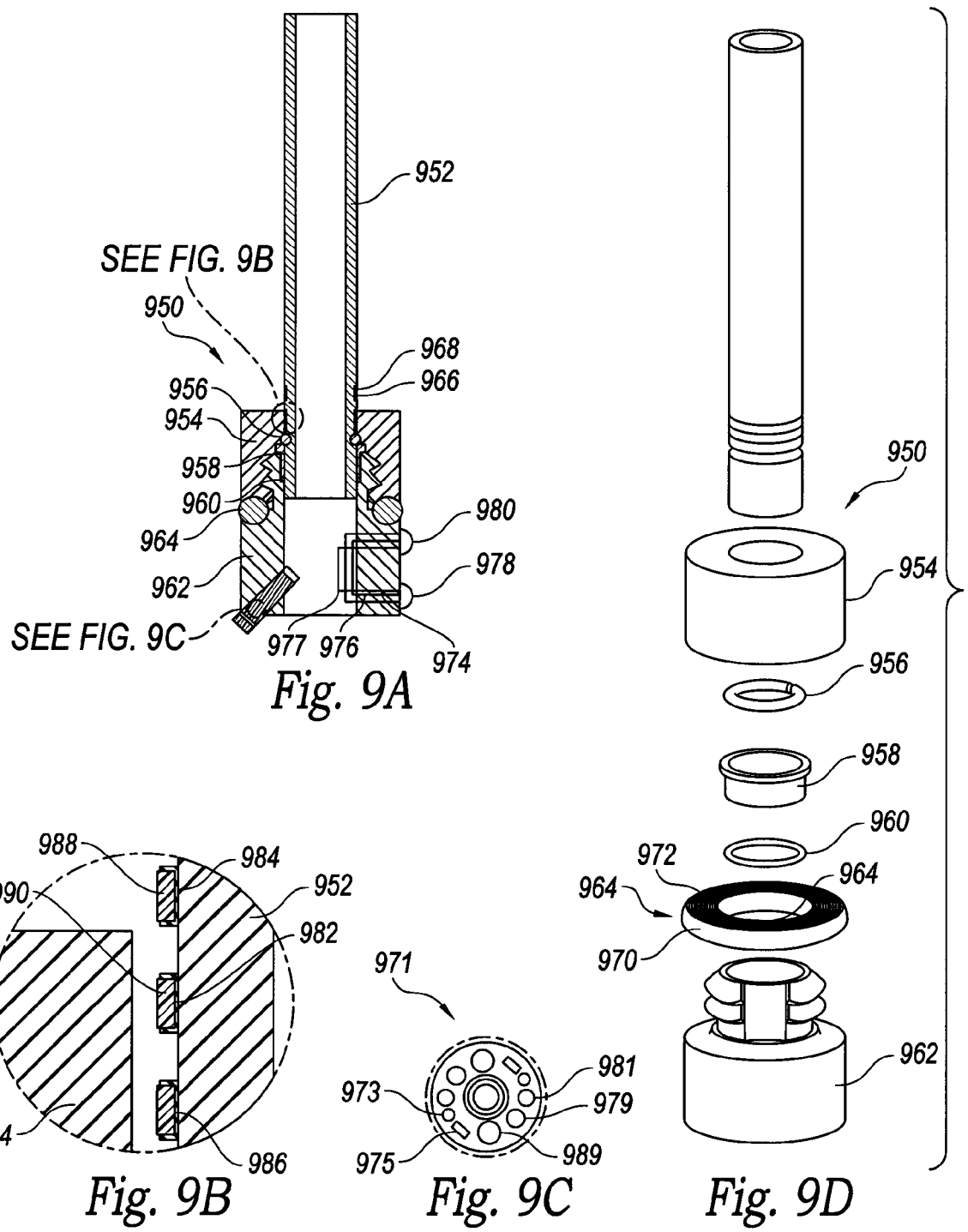
FIG. 9A is a side cross-sectional view of an assembly configured in accordance with yet another embodiment of the disclosure.
FIGS. 9B and 9C are enlarged detail views of portions of FIG. 9A.
FIG. 9D is an exploded view of the assembly of FIG. 9A.

FIG. 9A is a side cross-sectional view of an assembly 950 including one or more detectors, indicators, sensors, etc. configured in accordance with another embodiment of the disclosure. FIG. 9B is an enlarged view of detail D of FIG. 9A, and FIG. 9C is an enlarged view of detail C of FIG. 9A. FIG. 9D is an exploded view of the assembly 950 of FIG. 9A. Referring to FIGS. 9A-9D together, the assembly 950 includes a multifunction elastically deformable seal and status indicator 964, an elastomeric ring seal 960, a ring seal support 958, and a lock ring 956. Illustratively, as shown in FIGS. 9A and 9D, the annular seal 964 may be made of relatively soft closed cell sponge polymer with a generally oval cross-sectional shape before it is reformed into another cross section such as shown in FIG. 9A. An annular groove is provided in tube 952 to receive lock ring 956, which is restrained from expansion by an annular gland of nut 954 as shown. The seal support 958 rests against the nut 954 to support and urge the seal 960 to reform and seal against the annular gland of a fitting 962 and a tube 952 to provide an assured leak free seal that continues to perform even if support 958 is moved considerable axial distance as shown.

The status indicator 964 provides a means for one or more preventative maintenance signals the fitting 962 is axially displaced from the cap 954 thereby also causing axial displacement of the seal ring 960, the support 958, and/or the tube 952. Illustrative means for providing a preventative maintenance signal include the use of at least one different texture or color in different regions of the status indicator 964. For example, a first region 970 and/or and a second 972 can have different colors, such as white for region 970, and red for region 972. Thus if visual inspection detects a red color next to the white color on status indicator 964, the status indicator 964 is providing a signal or indication of a leak or other need for preventative maintenance.

Another suitable means for indicating a preventative maintenance signal consists of placing miniature, micro or nano circuitry at locations 982 and 984, as shown in FIG. 9B. One or more leak accumulators or concentrators 988, 990 provide signal magnification for early detection and activation of a maintenance request or alarm signal. Circuitry at 984 can be activated by a photovoltaic-powered circuit. Consequently if sensor circuits or detectors detect incipient leakage at locations 982 or 986, ambient light or an interrogation light source provides photovoltaic power to activate a radio signal or to serve in a circuit as a ring oscillator to develop an incipient leak signal that is broadcast or interrogated from the detector (s) by non-contact means such as radio wave or an infrared stimulator.

According to further embodiments of the disclosure, additional or backup locations for placement of miniature, micro or nano circuitry is shown at locations 966 and/or 968, which can be activated by a photovoltaic circuit. Consequently if a sensor circuit or detector senses incipient leakage at locations 966 and or 968, the detector can initiate a radio signal or trigger participation in a circuit as a ring oscillator to develop an incipient leak signal that is broadcast or interrogated by non-contact means such as radio wave or an infrared stimulator.

Additional embodiments of the disclosure directed to detecting incipient leakage with surface-active substances that enhance or depress the wettability of areas or regions where detection of a leak or other fluid properties is desired. In FIG. 9D, for example, applying hydrophobic substances and/or hydrophilic substances to the status indicator 964 (e.g., an o-ring) can provide a concentration of fluid at different locations on the status indicator 964. Indicators configured in accordance with these embodiments can use these different concentrations can to emit or otherwise generate a warning signal. More specifically, referring to the status indicator 964 of FIG. 9D, a hydrophobic substance can be applied at an external equatorial strip region or band 970 of the status indicator 964 to at least partially prevent incipient leak molecules from adhering to the band 970 (e.g., the band being "wetted" from the incipient leak molecules). Moreover, a hydrophilic substance can be applied to the remainder of the interior portion 972 of the status indicator 964 surrounding the band 970 to promote wetting of the interior portion 972 to enable numerous leak concentration and signal generation locations. In one embodiment, for example, in response to hydrophilic wetting the exterior band 970 and the interior portion 972 can provide a color change, release an odor or aromatic molecules that are more readily detectable by an odor detector in a sensor circuit 982 or 986 in response to parts per billion or parts per million concentrations on the hydrophilic detection surface, and/or provide electrical or electro-optical signal generation from the status indicator. As will be appreciated by one of ordinary skill in the relevant art, the portions of the status indicator 964 (or any other indicator disclosed herein) having different wettability characteristics are not limited to the configuration illustrated in FIG. 9D.

Another embodiment of the disclosure provides hydrophobic wetting capability similar to the minute fuzz (or other types of surface textures) that covers a peach that promotes wetting in some areas and prevents or inhibits wetting in other areas. More specifically, an indicator can include a surface having a texture or treatment that causes a fluid (e.g., water) to bead or wet in certain areas and prevent wetting in other areas to thereby concentration the rejected fluid for wetting an adjacent area. In this manner, the indicator can use the concentrated fluid to generate a maintenance signal at lower concentrations of incipient leakage molecules. In the Figures, for example, surface treatments of detectors at locations 966, 968, or on the status indicator 964 at locations 970 and/or 972, can include area having different wettability characteristics. In certain embodiments, for example, detectors or sensors at these locations can include hydrophobic dots that are adjacent to hydrophilic dots. In certain embodiments, for example, these regions can include a thin transparent film of titania that is exposed or otherwise receives ultraviolet interrogation light. In certain embodiments, activation with ultraviolet light provides wettability by alcohol, water and oils. Appropriate activation of the thin film of titania may thus produce a field of nanoscale domains where hydroxyl molecules become adsorbed to provide wettability for water and water solutions and the adjacent areas provide wettability for oils and oil solutions. The titania films according to these embodiments can be altered to react to specific stimuli. For example, the titania films may be doped with nitrogen, silver, silicon or other semiconductor enhancements to decrease the band gap and customize the interrogation light activation at a longer wavelength to provide an indication of incipient leakage and/or information regarding the types of molecules involved or other properties of a fluid.

According to another embodiment of the sensors or detectors disclosed herein, the detectors can concentrate portions of the fluid of interest with capillary wicking. For example, detectors or sensors configured in accordance with embodiments of the disclosure may include nano-wicking structures having closely spaced pores in such substrates as silica, titania, and carbon. Capillary wicking of leakage molecules of a fluid accumulates or concentrates them for more intense signal generation. For example, the concentrated fluid molecules can provide an enhancement of light reflectivity, transmissivity, or absorptivity as a characterizing type of signal discrimination, or alternatively anti-reflectivity as a discriminating means for development of signal generation. Concentrating or magnifying the presence of detectable molecules provides a very early indication of incipient leakage. Moreover, an intelligent interrogation procedure that takes leak-rate trend and ambient conditions into account enables much greater safety and assured confidence in systems that store and/or convey highly valuable, dangerous, objectionable, or annoying fluids.

Another application of the "watch-dog" or "traffic-cop" indicators and sensors disclosed herein for preventative maintenance provisions is to provide for identification, verification, and appropriate action or alarm procedures upon detection of specific ingredients or constituents of a fluid. For example, the sensors and detectors disclosed herein can detect specific ingredients in a fluid, such as critical components of a prescribed medication formula, or conversely, potentially harmful substances such as aflatoxins, mycotoxins, or ochratoxins in a fluid medium. In this instance a fluid conveyed by the conduit 952 is monitored by comparison of the UV, visible, and/or IR signal initiated at an emitter 978 and transmitted to a reader 980 that includes a miniature, micro, or nano radio transceiver to provide an appropriate function command or alarm. The emitter 978 and the transmitter 980 can be carried by the assembly 950. In certain embodiments, one or more fiber optic components or light pipes 974, 976, 977 can transmit an interrogation frequency between the emitter 978 and the transceiver 980. The light pipes 974, 976, 977 can incorporate selected surface materials with a known index of refraction and/or other optical properties that provide signal generation by adherence or adsorption of certain molecules that are being monitored in the fluid. Comparative analysis of the rate that optical properties change provides an analytical or inferred determination of the concentration of monitored molecules in the fluid medium under surveillance. Numerous different selective surfaces may be provided at different locations or on separate fiber optic components 974, 976, 977. In some instances, the fluid being delivered by conduit 952 may be slowed or stopped by a valve such as 951 (FIG. 9F) to provide time for signal intensification of the monitored substance. Comparison of the diffusion pattern, attenuation, enhancement, or reinforcement of selected radiation frequencies that are used as interrogation signals in the light pipes 974, 976, 977 enable identification, verification and appropriate action or alarm procedures.

Figure 9E:
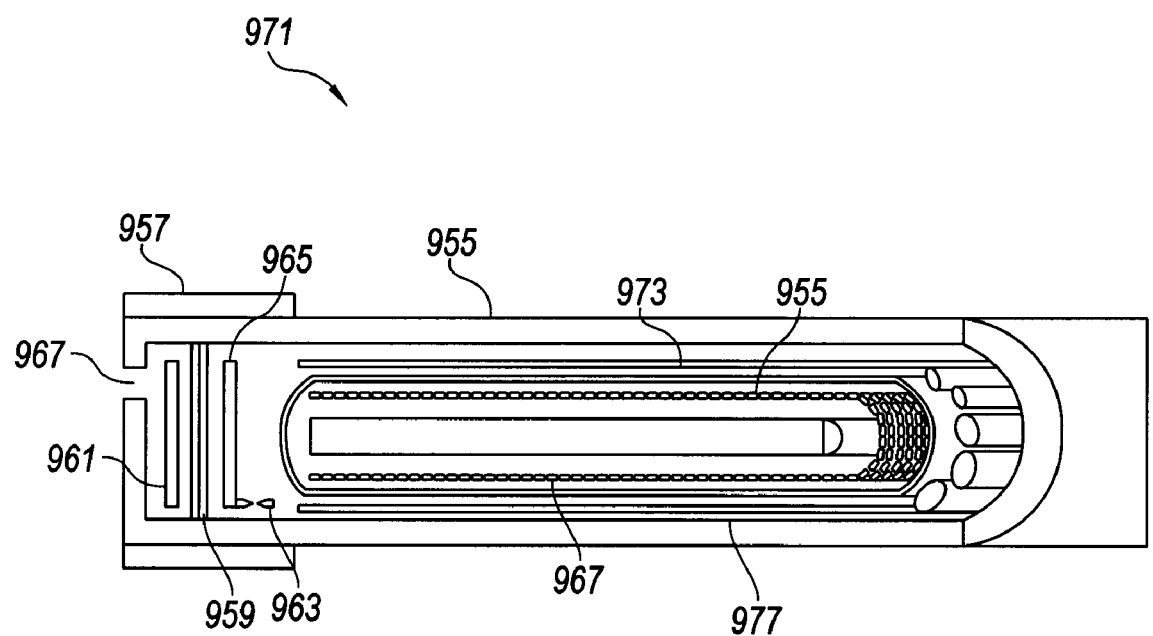
FIG. 9E is a side partial cross-sectional view of a system configured in accordance with embodiments of the disclosure.
Figure 9F:
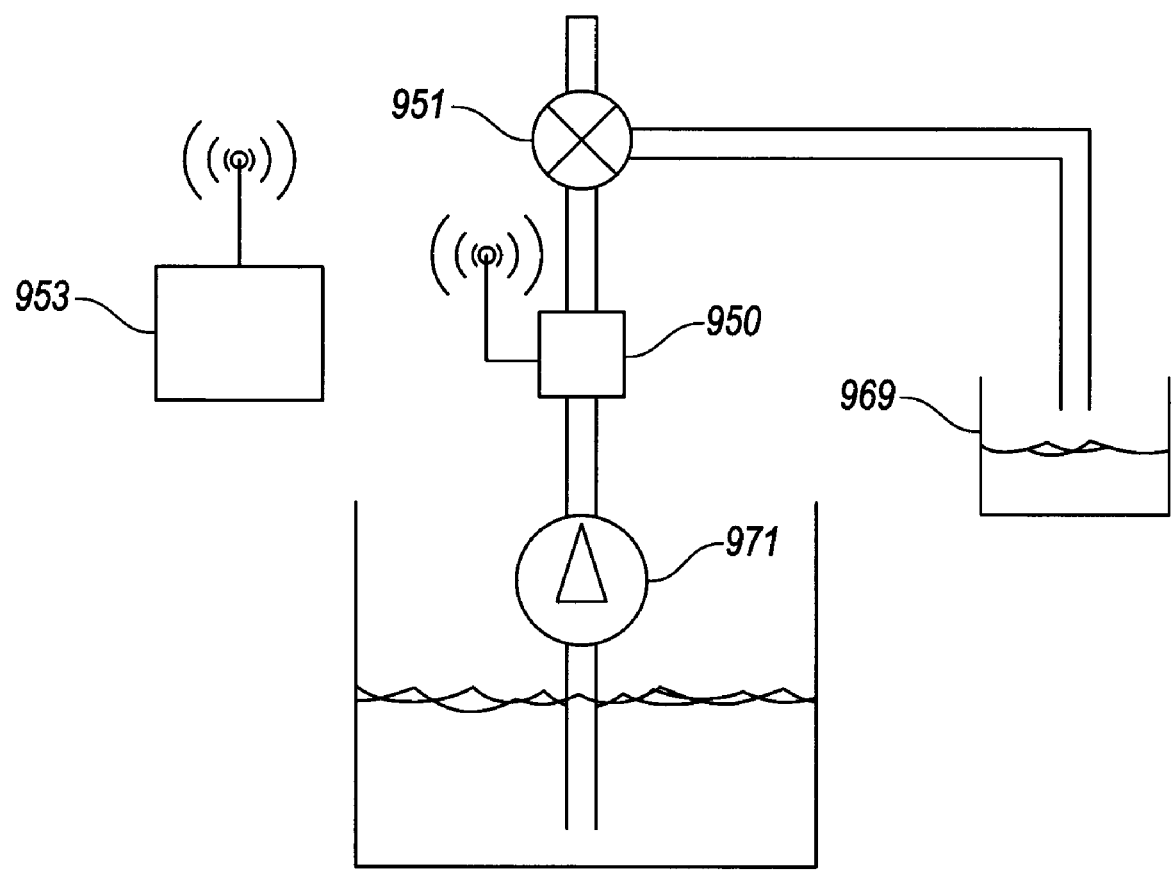
FIG. 9F is a schematic view of an environment for use with a detector configured in accordance with an embodiment of the disclosure.

FIG. 9C is an enlarged cross-sectional side view of a tubular system 971 carried by the assembly 950 shown in FIG. 9A, FIG. 9E is a side cross-sectional view of the tubular system 971, and FIG. 9F is a schematic view of an environment for use with a detector 950 configured in accordance with an embodiment of the disclosure. Referring to FIGS. 9C, 4E, and 9F together, in another embodiment a fluid sample in the conduit 952 is admitted in the tubular system 971 including a selection of capillaries 971, 973, 975, 989, 979, 981, etc., having various surface treatments, geometries, shapes, and dimensions as shown in detail in FIG. 9C. Molecules of a specific interest, such as an intended or adverse agent including, for example, the analyte family of poisons are selectively identified after being sequestered in such capillaries 971, 973, 975, 989, 979, 981 from a fluid such as water, milk, or soymilk by appropriate methods such as those disclosed in U.S. Pat. Nos. 4,859,611; 4,181,853; 5,178,832; or U.S. patent application Ser. No. 10/245,758, each of which is incorporated herein by reference in its entirety. Between cyclic sequestration and indication of monitored substances or molecules, the capillaries 971, 973, 975, 989, 979, 981 can be cleared by admission of an appropriate cleaning solvent and/or by expulsion with hydrogen and/or oxygen. For example, depending upon preferences regarding the monitored substance, such hydrogen and/or oxygen may be generated by miniature electrolysis cell 961 or by a larger electrolysis cell or another storage provision that delivers pressurized hydrogen and/or oxygen into the capillaries 971, 973, 975, 989, 979, 981.

FIG. 9C shows the enlarged cross section of the tubular system 971 with illustrating the capillaries 971, 973, 975, 989, 979, 981 of various sizes and shapes. FIG. 9E illustrates a longitudinal section of the tubular packaging arrangement of system 971, and includes a photovoltaic semiconductor 957 or some other suitable source of electricity to power the testing procedures performed by system 971. In the system 971, fluid samples travel various distances in the capillaries 971, 973, 975, 989, 979, 981 depending upon the viscosity, surface tension, and wettability produced by the material selection, dimensions, geometry and coatings that may be applied to the capillaries 971, 973, 975, 989, 979, 981. One or more detectors 967, such as photo-optic readers and/or sensors, can contact the sample fluid to identify and report by wireless communication to a controller 953 (FIG. 9F) which includes a wireless relay or transponder for producing the appropriate alarm, fail-safe activity, or verification information.

In instances that expedited clearing of 971, 973, 975, 989, 979, 981 is advantageous, for example as part of a quick cycle for fail-safe monitoring, a mixture of hydrogen and oxygen can be produced by an electrolyzer 961, ignited by application of a spark plasma at 963, and combusted to provide a rapid pressure rise and purging of the capillaries 971, 973, 975, 989, 979, 981. Such mixtures may be provided by mixing the outputs of the anode and cathode of the electrolyzer 961, or by reversing the voltage applied to the electrodes of the electrolyzer 961 to alternately produce hydrogen and oxygen. Controlling the time and current magnitude during such voltage reversals provides control of the proportions of oxygen and hydrogen in the mixture that is formed. Moreover, isolating one of the electrodes from participation in the purging operation by a separator membrane 959 enables such occasionally reversed voltage and current application to the other electrode 965 to provide mixtures that may be stoichiometric or enriched with hydrogen or oxygen for purposes such as reducing the peak combustion temperature, providing neutral, oxygen-rich oxidizing steam, or hydrogen-rich reducing steam for specific cleaning performances during the purging operation of the capillaries 971, 973, 975, 989, 979, 981.

If a more or less stoichiometric mixture of hydrogen and oxygen is combusted, a small amount of water may be formed and expelled and condensed mostly in the fluid within the conduit 952 and the vacuum that is created in cleared capillaries 971, 973, 975, 989, 979, 981 by the phase change contraction and resulting volumetric shrinkage provides rapid reloading of monitored substance samples. In instances where oxygen remains in the capillaries, hydrogen may be generated and combined with such oxygen to form steam. If hydrogen remains in the capillaries, oxygen may be generated and combined with such hydrogen to form steam in a procedure to standardize or normalize the test cycle.

Referring to FIG. 9F, which shows a compressor or pump 971, the conduit 952, the tattletale fitting indicator 950, the controller 953, a valve 951, and delivery to collector 969. In the illustrated embodiment, if detectors or sensors 950 indicate a threshold concentration of a leak, an unwanted substance, or any other property of a fluid flowing through the conduit 952, the detector 950 can generate an alarm so that the flow through conduit 952 may be stopped or diverted into a collection conduit by valve 951 as shown in FIG. 9F. In certain embodiments, the indicator 950 can wirelessly transmit the signal or alarm to the controller 953. This provides protection and/or sample collection for various purposes including removal, later reference, and/or validation testing.

Figure 10:
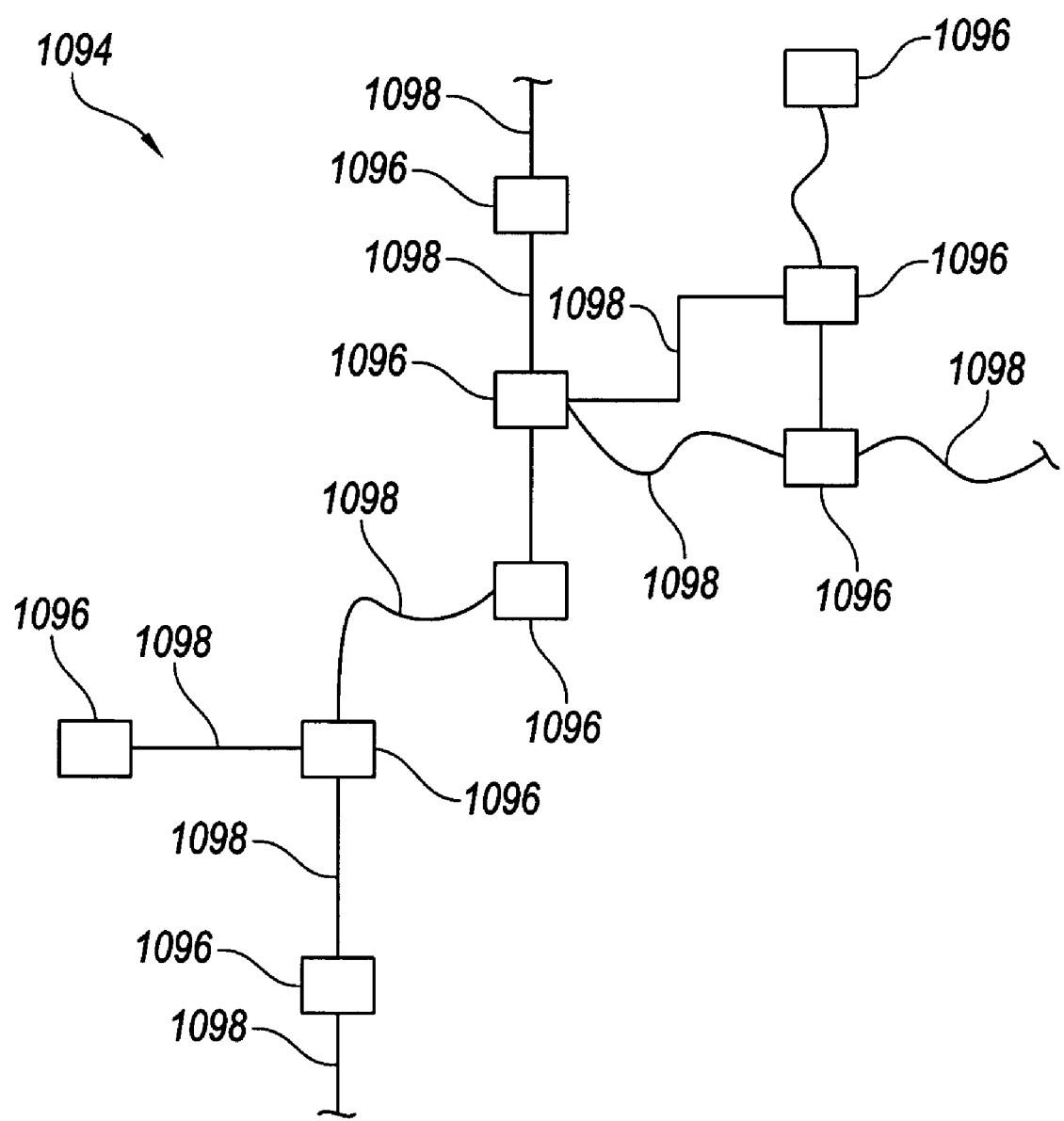
FIG. 10 is a schematic diagram of a fluid conduit system configured in accordance with an embodiment of the disclosure.

FIG. 10 is a schematic diagram of a fluid conduit system 1094 configured in accordance with an embodiment of the disclosure. In the illustrated embodiment, the system 1094 includes a plurality of fluid conveying conduits 1098 that are joined to one another with corresponding fitting assemblies 1096. The fitting assemblies 1096 can also cap the end of a conduit 1098. The fitting assemblies 1096 in the illustrated system 1094 can be generally similar to the fitting assemblies and associated components described above with reference to FIGS. 7A-9F, and/or include any of the features of the Tattletale embodiments described herein. For example, the fitting assemblies 1096 can include a male connector having retention features that rotatably engage corresponding engagement features of a female connector. According to another feature of the illustrated system 1094, the conduits 1098 can be generally straight or curved conduits. For example, the generally straight conduits 1098 can include hard drawn tubes or pipes, and the curved conduits 1098 can include annealed or soft tubes or pipes, or other flexible types of conduits. The conduits 1098 of the illustrated embodiment can be configured to be suitable for conveying or transporting various types of fluids (e.g., liquids, gases, etc.), for covering electrical cables or lines, or for any other application where conduits are commonly used. Moreover, the conduits 1098 can be made from metallic, plastic, or any other suitable material.

Figure 11:
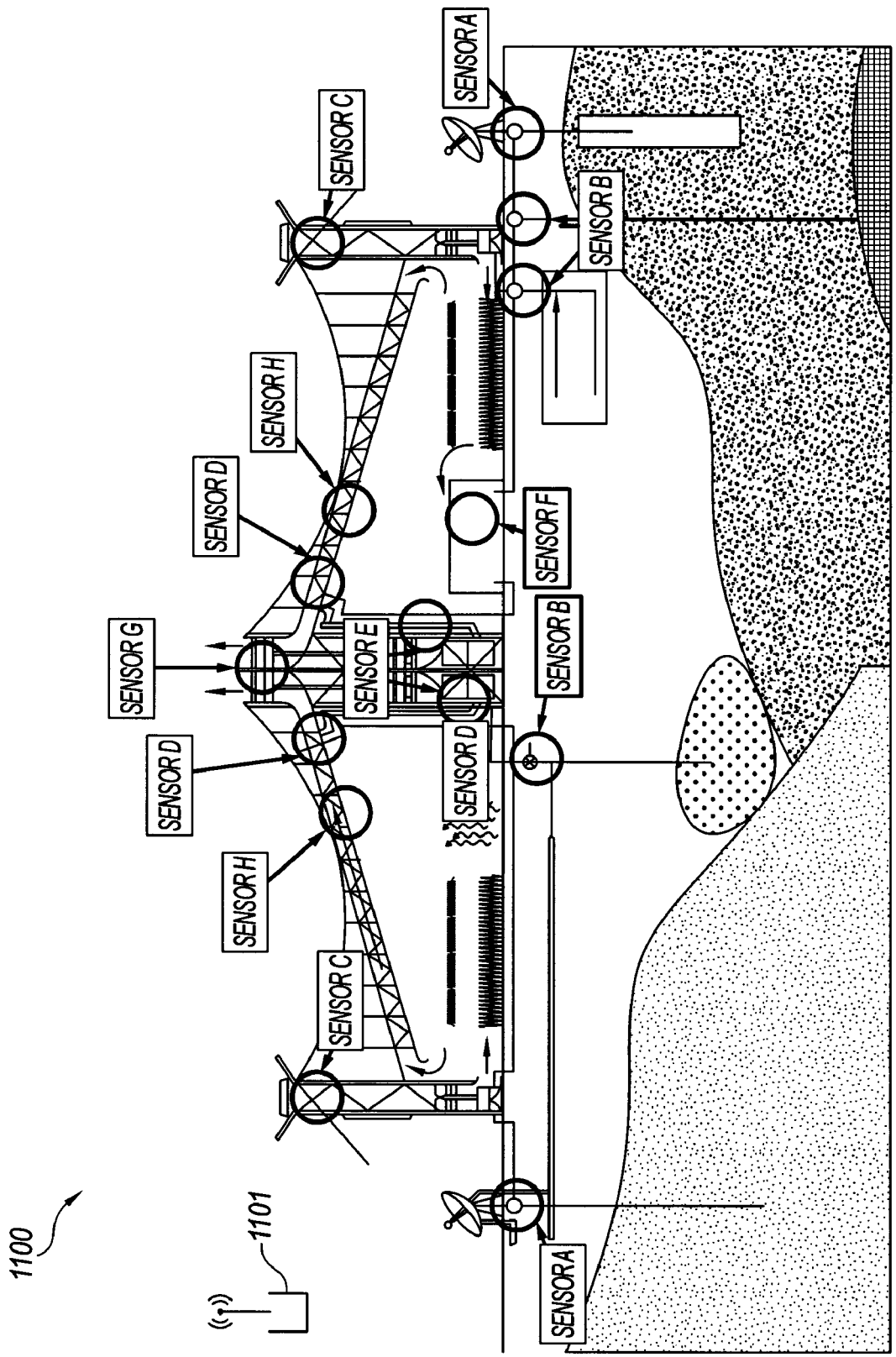
FIG. 11 is a schematic view of energy production installation configured in accordance with an embodiment of the disclosure.

FIG. 11 is a schematic view of energy production installation 1100 configured in accordance with an embodiment of the disclosure. As shown illustratively in FIG. 11, the installation includes various sensors configured in accordance with embodiments of the present disclosure (i.e., sensors configured to collect a target sample, detect or analyze properties of the target sample, report an indication of the analysis or detection, and/or clear the target sample) can be combined to provide quality control and assurance of components of an overall system. For example, sensors A-H may be disturbed at various locations within a full spectrum energy system as disclosed, for example, in U.S. Provisional Patent Application No. 61/237,479 entitled "Full Spectrum Energy," filed Aug. 27, 2009, which is incorporated by reference herein in its entirety. As shown in FIG. 11, the sensors A-H may be remotely monitored and controlled by central control unit 1101. According to one embodiment, sensors A-H may monitor the following system characteristics: Sensor A is monitoring the characteristics of working fluid(s) (temperature, gaseous/liquid state, fluid composition, etc.) at the site of solar thermal devices adding solar heat to hydrogen donor; Sensor B is monitoring characteristics of working fluid(s) (temperature, gaseous/liquid state, chemical content, etc.) of working fluids moving into and out of geothermal storage; Sensor C is monitoring characteristics of working fluid(s) (temperature, humidity, etc.) entering the system; Sensor D is monitoring characteristics of working fluid(s) (temperature/energy etc.) at heat exchangers; Sensor E is monitoring characteristics of working fluid(s) in the exhaust stream of internal combustion engines at the insulated exhaust pipes; Sensor F includes multiple sensors within an electrolyzer monitoring characteristics of working fluid(s) (temperature, gaseous/liquid state, fluid composition, chemical content, etc.); Sensor G is monitoring characteristics of working fluid(s) (temperature/energy, humidity, etc.) in the updraft conduit at the site of turbines; and Sensor H is monitoring characteristics of working fluid(s) (temperature, humidity, gaseous content, etc.) in agricultural micro-climates.

Figure 12:
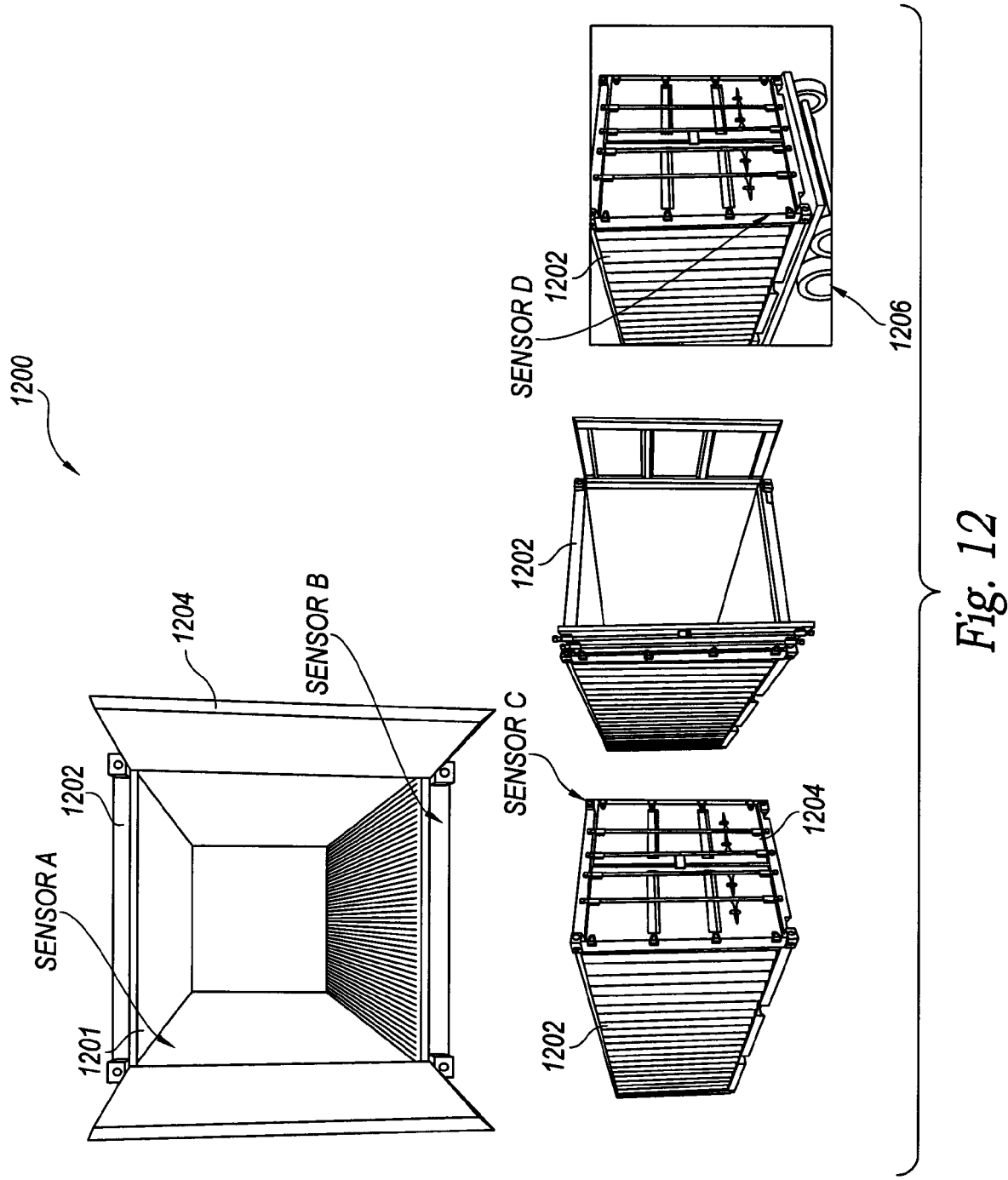
FIG. 12 illustrates yet another environment which incorporates sensors in accordance with another embodiment of the disclosure.

FIG. 12 illustrates yet another environment or networked system 1200 that incorporates sensors as disclosed herein. As shown in FIG. 12, sensors can be related to chemical surveillance and security tracking of shipping containers 1202 for trucking, railroads, marine shipping, and the like. For example, the sensors can monitor shipping transport means for drugs, hazardous materials, and/or other properties of shipped materials. Moreover, the sensors can be positioned throughout various international shipping containers and/or vehicles including, for example, land based (e.g., trucking, railway, etc.), marine, and/or air transportation vehicles. According to one embodiment, the system 100 can include Sensor A which can be located visibly or invisibly within the wall 1201 of a shipping container. Sensor A can signal if it has been tampered with or if its status has integrity. Sensor A can also differentially hold a record of how often and when the doors were opened, as well as providing an indication if target contents were removed. Target contents can be chemically tagged so that only Sensor A is able to detect the corresponding chemical tags. According to one aspect, Sensor A can also identify if human smuggling is taking place. Alternatively, Sensor A can identify if drugs are being shipped. Sensor B shows the sensor located proximate to a door 1204 when the door 1204 is in a closed position, and can accordingly used as an anti-tampering report in real-time when the door is opened and the seal is broken. Sensor C shows the sensor at the seal of a door 1204, and can be used, for example, as an anti-tampering report in real-time when the door is opened and the seal is broken. Sensor D shows the sensor placed at the interface of a shipping truck 1206 (railway car, marine or boat conveyance, etc.) and the container 1200. The Sensor D can accordingly report in real-time if the seal is broken, as well as chemically sensing and reporting in real-time if the container 1202 is exposed to any hazards from outside.

Figure 13:
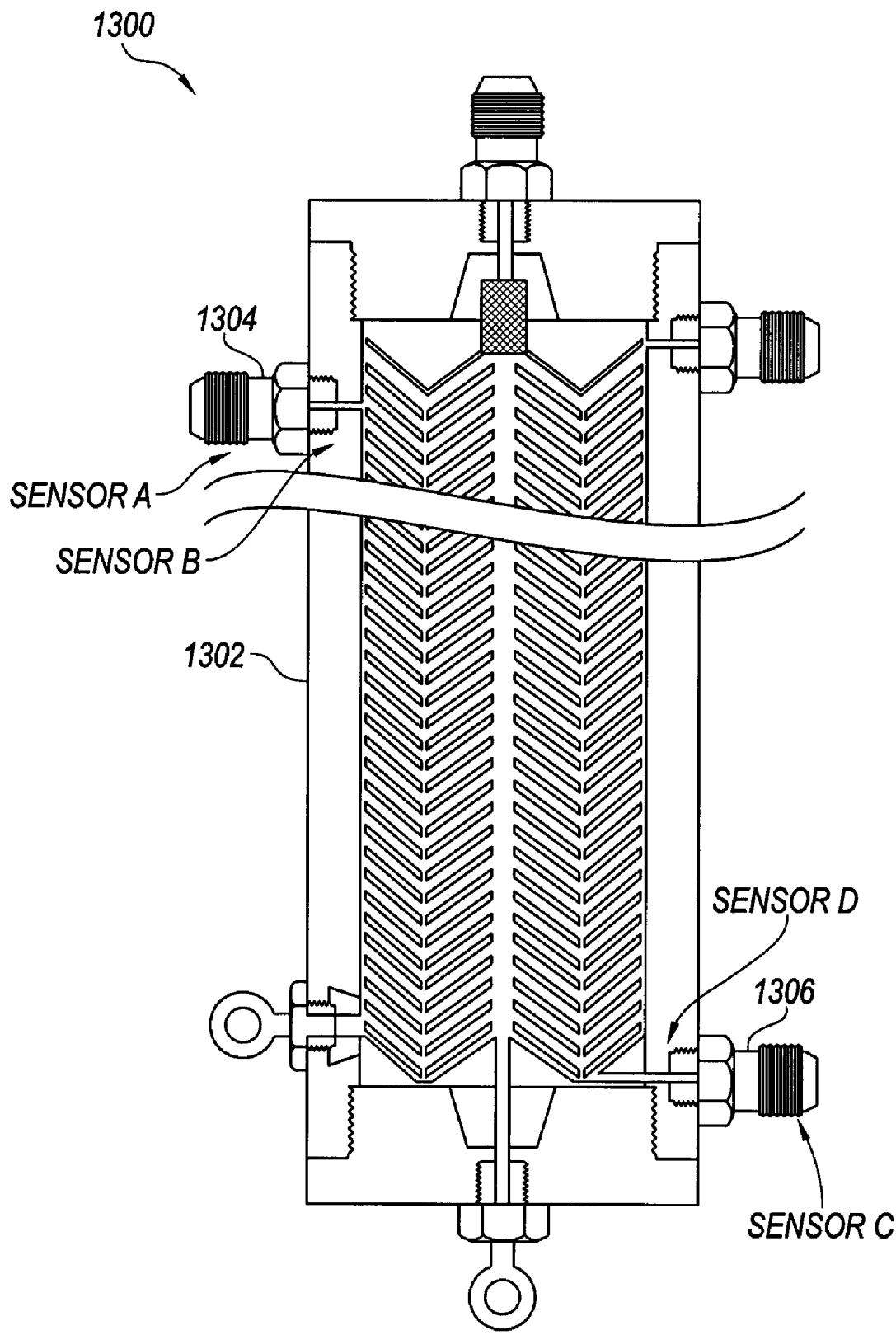
FIG. 13 illustrates an electrolytic cell which incorporates sensors in accordance with another embodiment of the disclosure.

FIG. 13 illustrates an electrolytic cell in accordance with co-pending applications disclosed and incorporated by reference above having at least one sensor in accordance with the present disclosure incorporated herein. In the illustrated embodiment, for example, the electrolytic cell 1300 can include Sensor A, which is positioned outside the vessel 1302 monitoring a first fluid connector 1304; Sensor B, which is positioned inside the 1302 vessel for monitoring an electrolyte flow into the vessel at an upper portion of the vessel; Sensor C, which is positioned outside the vessel 1302 for monitoring a second connector 1306; and Sensor D, which is positioned inside the vessel 1302 for monitoring the electrolyte flow from the vessel at the lower portion of the vessel.

In operation, Sensors A and C are connector-sensors that watch for fluid leaks at high pressure to provide early warning of incipient leaks. As such, Sensors A and C can be used to monitor the integrity of the high pressure system. Sensors B and D can be fluid-sensors (e.g., sensor for liquids and/or gases) that differentially monitor and provide feedback on the chemical contents within the electrolyzing vessel at various locations. Although only four sensors are schematically shown in FIG. 13, in further embodiments the electrolytic cell 1300 can include more than four sensors at various locations on the inside and outside of the vessel 1302.

Similar to the embodiment described above with reference to FIG. 13, in additional embodiments sensors can be networked or otherwise positioned throughout a process line or manufacturing line to monitor the integrity of the line or system. For example, the networked sensors can be positioned throughout various suitable processing lines including, for example, chemical processing lines, pharmaceutical processing lines, gas processing lines or pipelines, water or other fluid processing lines. Moreover, the chemical surveillance and/or identification in these and other systems can interface with radio frequency identification (RFID) systems, global positioning systems (GPS), and/or inertial tracking systems to provide robust and strengthened security and tracking systems.

Additional systems, assemblies, methods, components and other features configured in accordance with embodiments of the present disclosure can include any of the following examples. One example is directed to a fitting assembly for attachment to an end portion of a conduit, the fitting assembly comprising: a first component configured to receive the end portion of the conduit; a second component operably coupled to the first component, wherein the second component engages the first component to retain the end portion of the conduit in the first component, and an indicator carried by at least one of the first and second components, wherein the indicator provides an externally accessible indication of information related to a fluid flowing through the fitting assembly.

In the fitting assembly the indicator can be a first leak indicator, and the fitting assembly can further comprise a plurality of leak indicators at different positions on the fitting assembly. Also, the first leak indicator can provide a first type of indication that differs from a second type of indication provided by a second leak indicator. Moreover, the indicator can be positioned to contact an exterior surface of the end portion of the conduit when the first component receives the end portion of the conduit. In addition, the indicator can be configured to chemically react with a fluid flowing through the fitting assembly when the fluid contacts the indicator. In some embodiments, the indication of information can include a visual indication of fluid leakage, a release of a liquid from the indicator. The liquid can have a first color that differs from a second color of the fluid flowing through the fitting assembly. Moreover, the indicator can react with the fluid flowing through the fitting assembly to provide the visual indication. In addition, the indication of information can include includes at least one of a visual indication released by the indicator, an odor emitted by the indicator, and a radio signal transmitted by the indicator. The indication of information can also be responsive to at least one of visible radiation, ultraviolet radiation, and microwave radiation directed at the fitting assembly, and/or include a radio signal emitted by the indicator. The radio signal can be provided in response to a change in at least one of capacitance, resistance, and magnetic field of the leak detector caused by a fluid flowing through the fitting assembly. Moreover, the indicator can include comprises circuitry configured to sense fluid leakage, and wherein the indication of fluid leakage includes a radio signal emitted by the circuitry of the indicator. Also, the fitting assembly can further include a power source operably coupled to the detector. The power source can be a photovoltaic power source that is responsive to an external stimulus directed at the fitting assembly. Moreover, the indication of information can include a signal emitted by the indicator, wherein the signal includes information related to at least one of an amount of fluid leakage, the location of the fluid assembly, and the time of fluid leakage. The indicator can further include a hydrophobic portion and a hydrophilic portion, and the conduit can be configured to transfer water, and the hydrophilic portion of the leak detector can concentrate portions of water that contact the indicator to magnify the presence of the water on the leak detector. In addition, at least a portion of the indicator includes titania, as well as a capillary assembly configured to concentrate at least a portion of the fluid.

In other embodiments, a fitting assembly can include: a first member configured to receive a portion of a fluid conveying conduit; a second member configured to engage the first member to secure the portion of the conduit within the first member, wherein the second member is axially aligned with the first member; and a seal engaged with the first and second members, wherein the seal provides a visual indication of an axial position of the first member relative to the second member. The seal can comprise an annular ring positioned between the first and second members, and the annular ring can include a first portion with a first color and a second portion with a second color different than the first color. Moreover, the first portion can be located at an outer strip region extending circumferentially around the annular ring, and the second portion can generally surround the first portion. Also, only the first color can be visible when the first member is at a first axial position relative to the second member, and both of the first and second colors can be visible when the first member is axially spaced apart from the first axial position away from the second member. Furthermore, only the first color can be visible when the first member is at a fluid-tight connection location with reference to the second member, and the first and second colors can be visible when the first member is positioned at a non-fluid-tight connection location with reference to the second member. In addition, the fitting assembly can further comprise a leak detector carried by at least one of the first and second components, wherein the leak detector provides an indication of a leak from the fitting assembly if the leak detector comes into contact with a fluid flowing through the fitting assembly. The indication of a leak can include a colored liquid released from the fitting assembly in response to the contact from the fluid flowing through the fitting assembly. Moreover, the leak detector can react with the fluid flowing through the assembly and change a color of the fluid that contacts the leak detector. The indication of a leak can also include a radio signal emitted from the leak detector. The leak indicator can also be responsive to a stimulus directed at the leak indicator. The stimulus can include at least one of visible radiation, ultraviolet radiation, and microwave radiation. Moreover, the seal can be a first seal, and the fitting assembly can further comprise: a second seal axially spaced apart from the first seal; a seal support member positioned proximate to and in contact with the second seal; and a leak detector carried by at least one of the first and second members, wherein the leak detector is configured to provide an indication of the fluid leakage from the fitting assembly past the second seal.

A method of determining the early stages of a leak in a fitting assembly can include: providing a conduit for conveying a fluid; attaching a fitting assembly to the conduit, wherein the fitting assembly comprises a first component coupled to the conduit, a second component configured to engage the first component to retain the conduit within the first component, and a leak detector carried by at least one of the first and second components; and flowing the fluid through the conduit and the fitting assembly, wherein if the fluid contacts the leak indicator the leak detector provides a warning in response to a fluid leakage from the fitting assembly. The method can also include providing a stimulus to the leak detector while flowing the fluid through the conduit. Providing the stimulus can include directing at least one of visible radiation, ultraviolet radiation, and microwave radiation at the leak detector, and wherein the stimulus magnifies the warning. Moreover, the warning can comprise a visual indication of the fluid leakage. Attaching the fitting assembly with the leak detector can further include providing a sensor circuit carried by the fitting assembly, and wherein the warning includes a radio signal emitted from the sensor circuit.

Another embodiment of a fluid conduit system can comprise: a first conduit configured for conveying a fluid; a second conduit configured for conveying the fluid; and a fitting assembly configured for coupling the first conduit to the second conduit for conveying the fluid there between, wherein the fitting assembly comprises—a first component configured to be attached to at least one of the first and second conduits; a second component carried by the first component, wherein the second component engages the first component to retain the at least first and second conduit; and a leak indictor carried by at least one of the first and second components, wherein the leak indicator provides a warning if the fluid leaks from the fitting assembly between the first and second conduits. The first component can be a body having a first end portion opposite a second end portion, the first end portion being coupled to the first conduit and the second end portion being coupled to the second conduit; and the second component can be a sleeve that is axially aligned with the body and disposed over at least a region of one of the first and second end portions. The leak indicator can be positioned to contact at least one of the first and second conduits. Moreover, the warning can include a visual indication that is externally accessible from the fitting assembly. In additional embodiments, the warning includes a radio signal transmitted from the fitting assembly to provide an alert to the fluid leakage. Also, the warning can be received in response to an interrogation stimulus directed at the fluid conduit assembly. The interrogation stimulus can include at least one of visible radiation, ultraviolet radiation, microwave radiation, infrared radiation, and a radio signal. Moreover, the first and second conduits can be a first set of conduits and the fitting assembly can be a first fitting assembly associated with the corresponding first set of conduits, and the fluid conduit assembly can further comprise: a plurality of sets conduits generally similar to the first set of conduits; and a plurality of fitting assemblies, wherein each fitting assembly is generally similar to the first fitting assembly, and wherein individual fitting assemblies are associated with a corresponding set of conduits.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

To the extent not previously incorporated herein by reference, the present application incorporates by reference in their entirety the subject matter of each of the following materials:

U.S. patent application Ser. No. 13/027,208, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS;

U.S. patent application Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS;

U.S. patent application Ser. No. 13/027,015, filed on Feb. 14, 2011 and titled CHEMICAL REACTORS WITH RE-RADIATING SURFACES AND ASSOCIATED SYSTEMS AND METHODS;

U.S. patent application Ser. No. 13/027,244, filed on Feb. 14, 2011 and titled THERMAL TRANSFER DEVICE AND ASSOCIATED SYSTEMS AND METHODS;

U.S. patent application Ser. No. 13/026,990, filed on Feb. 14, 2011 and titled CHEMICAL REACTORS WITH ANNULARLY POSITIONED DELIVERY AND REMOVAL DEVICES, AND ASSOCIATED SYSTEMS AND METHODS;

U.S. patent application Ser. No. 13/027,181, filed on Feb. 14, 2011 and titled REACTORS FOR CONDUCTING THER-

MOCHEMICAL PROCESSES WITH SOLAR HEAT INPUT, AND ASSOCIATED SYSTEMS AND METHODS;

U.S. patent application Ser. No. 13/027,215, filed on Feb. 14, 2011 and titled INDUCTION FOR THERMOCHEMICAL PROCESS, AND ASSOCIATED SYSTEMS AND METHODS;

U.S. patent application Ser. No. 13/027,198, filed on Feb. 14, 2011 and titled COUPLED THERMOCHEMICAL REACTORS AND ENGINES, AND ASSOCIATED SYSTEMS AND METHODS;

U.S. Patent Application No. 61/385,508, filed on Sep. 22, 2010 and titled REDUCING AND HARVESTING DRAG ENERGY ON MOBILE ENGINES USING THERMAL CHEMICAL REGENERATION;

U.S. patent application Ser. No. 13/026,060, filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; and U.S. patent application Ser. No. 13/027,214, filed on Feb. 14, 2011 and titled ARCHITECTURAL CONSTRUCT HAVING FOR EXAMPLE A PLURALITY OF ARCHITECTURAL CRYSTALS.

I claim:

1. A method for detecting the presence and/or properties of a target sample, the method comprising:
   selectively collecting a microscopic portion of a target sample with a sample collector;
   detecting, with the sample collector, at least one of the following—
      a presence of the microscopic portion of the target sample in the sample collector; and
      one or more properties of the microscopic portion of the target sample;
   reporting, from the sample collector, an indication of the detection of the one or more properties of the microscopic portion of the target sample; and
   at least partially removing the microscopic portion of the target sample from the sample collector wherein the sample collector is comprised of an architectural construct including spaced apart layers of matrix characterizations of a crystal.

2. The method of claim 1 wherein selectively collecting the microscopic portion comprises at least one of the following:
   filtering individual molecules of the target sample through corresponding layers of the architectural construct;
   absorbing individual molecules of the target sample between corresponding layers of the architectural construct;
   reflecting the microscopic portion of the target sample between corresponding layers of the architectural construct;
   drawing the microscopic portion of the target sample between corresponding layers of the architectural construct via capillary action; and
   inducing a pressure gradient that at least partially urges the microscopic portion of the target sample between corresponding layers of the architectural construct.

3. The method of claim 1 wherein detecting with the sample collector comprises at least one of the following:
   sensing a rate that the portion of the target sample loads between corresponding layers of the architectural construct;
   sensing a depth that the portion of the target sample loads between corresponding layers of the architectural construct;
   sensing at least one of a transmissivity, reflectivity, and refraction of the portion of the target sample between corresponding layers of the architectural construct; and
   sensing a wavelength shift of the portion of the target sample between corresponding layers of the architectural construct.

4. The method of claim 1 wherein reporting an indication of the detection of the one or more properties of the portion of the target sample comprises:
   emitting a radio signal with a nano-radio;
   generating an electrical current;
   providing a response to an interrogation signal; and
   providing a signal to a separate collector portion in a network of collector portions.

5. The method of claim 1 wherein at least partially removing the portion of the target sample comprises at least partially removing the portion of the target sample with the same method as selectively collecting the portion of the target sample.

6. The method of claim 1 wherein the sample collector is a first sample collector in a network of multiple sample collectors, and wherein the method further comprises performing the steps of collecting, detecting, reporting, and removing with the multiple individual sample collectors.

7. The method of claim 1, further comprising analyzing the one or more properties of the microscopic portion to determine one or more corresponding characteristics of the target sample.

8. A method comprising:
   collecting a microscopic portion of a target sample with a self-contained sensing component wherein the means for selectively collecting the portion of the target sample comprises an architectural construct including spaced apart layers of matrix characterization of a crystal that are configured to load individual portions of the target sample;
   automatically sensing at least one property of the collected microscopic portion of the target sample with the sensing component; and
   providing a real-time externally accessible indication of the at least one property from the sensing component.

9. The method of claim 8 wherein sensing the at least one property of the microscopic portion comprises:
   detecting a presence of the portion of the target sample; and
   analyzing one or more material properties of the target sample.

10. The method of claim 8, further comprising clearing at least a portion of the target sample from the sensing component and cyclically repeating the collecting, sensing, and providing an externally accessible indication.

11. The method of claim 8 wherein collecting a microscopic portion comprises collecting a molecular sized portion of the target sample, and wherein sensing the at least one property comprises sensing the at least one property from the molecular sized portion of the target sample.

12. The method of claim 8 wherein collecting a microscopic portion comprises accumulating a predetermined amount of the target sample sufficient to sense the at least one property of the target sample.

13. The method of claim 8 collecting a microscopic portion of the sample comprises collecting a microscopic portion of a sample in at least one of the following environments or systems: quality assurance, preventative maintenance, safety and hazard warnings, homeland security, and chemical surveillance.

14. A system comprising:
means for selectively collecting a portion of a target sample, wherein the portion is a microscopic portion relative to a size of the target sample wherein the means for selectively collecting the portion of the target sample comprises an architectural construct including spaced apart layers of matrix characterization of a crystal that are configured to load individual portions of the target sample;
means for automatically detecting the presence of one or more properties of the collected portion of the target sample;
means for automatically analyzing the one or more properties of the microscopic portion of the target sample; and
means for reporting an instantaneous indication of the analysis of the one or more properties of the target sample.

15. The system of claim 14, further comprising means for removing the portion of the target sample from the means for selectively collecting the portion of the target sample.

16. The system of claim 14 wherein the each of the means for selectively collecting, means for automatically detecting, means for automatically analyzing, and means for reporting are part of a first sensor, and wherein the system further comprises:
a plurality sensors each having the same features as the first sensor; and
a controller configured to communicate with at least one of the sensors.

17. The system of claim 16 wherein the plurality of sensors are distributed throughout at least one of the following environments: a public transportation system, a water supply or distribution system, a food production, packaging, or transport system, a natural gas pipeline distribution system, a medicine delivery system, and/or a chemical or pharmaceutical manufacturing system.

18. The system of claim 14 wherein the means for selectively collecting a portion of the target sample comprises means for accumulating one or more separate molecular-sized portions of the target sample.

* * * * *

UNITED STATES PATENT AND TRADEMARK OFFICE
CERTIFICATE OF CORRECTION

| | |
|---|---|
| PATENT NO. | : 8,312,759 B2 |
| APPLICATION NO. | : 13/027188 |
| DATED | : November 20, 2012 |
| INVENTOR(S) | : Roy Edward McAlister |

Page 1 of 1

It is certified that error appears in the above-identified patent and that said Letters Patent is hereby corrected as shown below:

On the title page, item (56), in column 2, under "Other Publications", line 1, delete "Untra-" and insert -- Ultra- --, therefor.

In the drawings:

On sheet 8 of 18, in Figure 6B, Box 652, line 1, delete "ENVIROMENT" and insert -- ENVIRONMENT --, therefor.

In the specification:

In column 11, line 59, delete "U U.S." and insert -- U.S. --, therefor.

In column 11, line 62, after "CRYSTALS,"" delete "filed concurrently herewith,".

In column 13, line 4, delete "and or" and insert -- and/or --, therefor.

In column 16, line 36, after "refraction" insert -- . --.

In column 23, line 44, delete "and or" and insert -- and/or --, therefor.

In column 34, line 45, delete "and or" and insert -- and/or --, therefor.

Signed and Sealed this
Eleventh Day of February, 2014

Michelle K. Lee
*Deputy Director of the United States Patent and Trademark Office*